US008163943B2

(12) United States Patent
Kobayashi et al.

(10) Patent No.: US 8,163,943 B2
(45) Date of Patent: Apr. 24, 2012

(54) EPOXYCARBOXAMIDE COMPOUND, AZIDE COMPOUND, AND AMINO ALCOHOL COMPOUND, AND PROCESS FOR PREPARING α-KETO AMIDE COMPOUND USING THEM

(75) Inventors: Nobuo Kobayashi, Sagamihara (JP); Tsuneo Koji, Hachioji (JP); Takashi Fujita, Nishitama-gun (JP); Tomofumi Nishimura, Tokai (JP); Akihiko Hosoda, Shiki (JP)

(73) Assignee: Seikagaku Kogyo Kabushiki Kaisha, Tokyo (JP)

( * ) Notice: Subject to any disclaimer, the term of this patent is extended or adjusted under 35 U.S.C. 154(b) by 949 days.

(21) Appl. No.: 11/981,120

(22) Filed: Oct. 31, 2007

(65) Prior Publication Data
US 2008/0064873 A1 Mar. 13, 2008

Related U.S. Application Data

(60) Division of application No. 10/331,702, filed on Dec. 30, 2002, now Pat. No. 7,326,799, which is a continuation-in-part of application No. PCT/JP01/05668, filed on Jun. 29, 2001.

(30) Foreign Application Priority Data

Jun. 30, 2000 (JP) ................. 2000-198089
Jun. 30, 2000 (JP) ................. 2000-198090
Jun. 30, 2000 (JP) ................. 2000-198091

(51) Int. Cl.
C07C 247/00 (2006.01)
C07C 261/00 (2006.01)
C07C 69/00 (2006.01)
C07D 317/44 (2006.01)
C07D 223/12 (2006.01)
C07D 223/04 (2006.01)

(52) U.S. Cl. .......... 552/12; 549/438; 549/439; 540/605; 540/606; 540/609; 560/115; 560/129

(58) Field of Classification Search ............ 552/10, 552/12; 544/148, 165; 548/536; 549/439, 549/548, 438; 540/609, 605, 606; 560/115, 560/129
See application file for complete search history.

(56) References Cited

U.S. PATENT DOCUMENTS

| 4,341,718 A | 7/1982 | Kim et al. |
| 4,849,531 A | 7/1989 | Haebich et al. |
| 5,714,471 A | 2/1998 | Rowe et al. |

FOREIGN PATENT DOCUMENTS

| DE | 3825242 | 2/1989 |
| EP | 672648 A1 | 9/1995 |
| EP | 0 792 876 | 9/1997 |
| EP | 1008592 A2 | 6/2000 |
| JP | 04-149166 | 5/1992 |
| JP | 04-211648 | 8/1992 |
| JP | 06-504547 | 5/1994 |
| JP | 7-228549 | 8/1995 |
| JP | WO-96/16079 | 5/1996 |
| JP | 11-292833 | 10/1999 |
| WO | WO-9212140 | 7/1992 |
| WO | WO-95/00535 | 1/1995 |
| WO | WO-96/20725 | 7/1996 |
| WO | WO-9816512 | 4/1998 |
| WO | WO-99/17778 A1 | 4/1999 |

(Continued)

OTHER PUBLICATIONS

Pearson et al., Journal of Organic Chemistry (1989), 54(17), 4235-7.*

(Continued)

*Primary Examiner* — Taylor Victor Oh
(74) *Attorney, Agent, or Firm* — Jordan and Hamburg LLP

(57) ABSTRACT

The present invention is to provide manufacturing intermediates which can be led to useful α-ketoamide compounds having protease-inhibiting activity extremely economically and stereoselectively, and to provide epoxycarboxamide compounds, azide compounds and amino alcohol compounds represented by the following formulae:

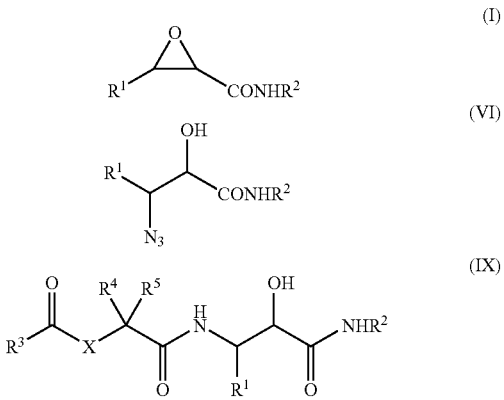

wherein $R^1$ and $R^2$ each represents alkyl group, alkenyl group, aromatic hydrocarbon group or heterocyclic group; $R^3$ represents alkyl group, alkenyl group, aromatic hydrocarbon group, heterocyclic group, $R^6$—O— or $R^7$—N($R^8$)—; where $R^6$ represents alkyl group, alkenyl group, aromatic hydrocarbon group or heterocyclic group; $R^7$ and $R^8$ each represents hydrogen atom, alkyl group, alkenyl group, aromatic hydrocarbon group or heterocyclic group, and, $R^4$ and $R^5$ represent the same groups as $R^7$ and $R^8$, respectively, and $R^4$ and $R^5$ optionally form a ring together; and X represents —O— or —N($R^9$)—, where $R^9$ represents hydrogen atom or alkyl group, and X optionally forms a ring together with $R^4$ or $R^5$,
and processes for preparing α-keto amide compound using the same.

11 Claims, No Drawings

FOREIGN PATENT DOCUMENTS

| | | |
|---|---|---|
| WO | WO-00/52032 A1 | 9/2000 |
| WO | WO-01/40262 A1 | 6/2001 |

OTHER PUBLICATIONS

Matsuura et al., Peptide Chemistry (1995), Volume Date 1994, 32nd, 41-4 (Abstract).*

Behrens et al , Selective transformations of 2,3-epoxy alcohols and related derivatives. Strategies for nucleophilic attack at carbon-3, or carbon-2, Journal of Organic Chemistry , 1985, 50(20), p. 5696-5704.*

Jan. 1, 1997 "The synthesis of lysine .alpha.-ketoamide thrombin inhibitors via an epoxy amide ring opening" Cacciola, J., Alexander, R.S., Fevig, J. M., Stouten, P. F. W., vol. 38, No. 33 5741 to 5744.

Jan. 1, 1985 "Nucleophilic Openings of 2,3-Epoxy Acids and Amides Mediated by Ti(O-i-Pr)4 Reliable C-3 Selectivity" J. Michael Chong et al. J. Org. Chem. vol. 50 pp. 1560-1563.

Jul. 31, 1984 Selective Transformations of 2,3-Epoxy Alcohols and Related Derivatives. Strategies for Nucleophilic Attack at Carbon-3 or Carbon-2 Carl H. Behrens et al. J. Org. Chem. vol. 50 pp. 5696-5704.

Dec. 31, 1989 "A Convenient Synthesis of Enantiomerically Pure (2S,3S)- or (2R,3R)-3-Hydroxyleucine" Charles G. Caldwell et al. Synthesis pp. 34-36.

Jun. 12, 1996 "A Cobalt Catalyzed Protocol for the Synthesis of Substituted B-Phenyl Isoserine Derivatives" Beena Bhatia et al. Tetrahedron Letters vol. 37 pp. 7311-7314.

May 19, 1997 "Diastereoselective alpha-Iodination Reaction of 4-Alkenyl amide Having a beta-chiral center" Okada M. et al. Tetrahedron vol. 53, No. 20 pp. 6825-6834.

May 2, 1997 "Tryptamine derived amides from clausena indica" Riemer B. et al. Phytochemistry, Pergamon Press, GB vol. 45, No. 2 pp. 337-341.

Jul. 23, 1999 "Synthesis of Optically Active 1,4-Benzoxazinones and 1,5-Benzoxazepinones by Regiocontrolled Ring Transformations of Oxirane Carboxylic Acids and Esters with Aromatic o-Hydroxyarylamines" Woydoowski K. et al. Tetrahedron, Elsevier Science Publishers, Amsterdam, NL vol. 55, No. 30 pp. 9205-9220.

Jan. 1, 1984 "Asymmetric hydrogenation catalyzed by (achiral base) bis(dimethylglyoximato)cobalt(II)-chiral cocatalyst system" Takeuchi S. et al. Bulletin of the Chemical Society of Japan vol. 57, No. 7 pp. 1920-1928.

Jan. 1, 1985 "Reactions of 3-phenylglycidic esters" Hashiyama T. et al. Chemical and Pharmaceutical Bulletin vol. 37, No. 40 pp. 2348-2358.

Apr. 21, 1967 "Mass Spectrometric Studies. Beta-phenyglycidic esters and amides" Baldas J. et al. Australian Journal of Chemistry vol. 20, No. 12 pp. 2664-2668.

Jan. 1, 1987 "Cyclofunctionalisation of epoxyalcohol derivatives" McCombie S.W. et al. Tetrahedron Letters vol. 28, No. 4 pp. 383-386.

Jan. 1, 1988 "Studies on aziridine derivatives. III. Synthesis and immunopharmacologial activity of aziridine derivatives of propionic acid" Kowalczyk-Bronisz S.H. et al. Archivum immunologiae et Therapiae Experimentalis vol. 36, No. 3 pp. 249-267.

1996, "Novel Peptidyl alpha-Keto Amide Inhibitors of Calpains and other Cysteine Proteases" Li et al. J. Med. Chem. vol. 39 pp. 4089-4098.

1993, "Peptide alpha-Keto Ester, alpha-Keto Amide, and alpha-Keto Acid Inhibitors of Calpains and Other Cysteine Proteases" Li et al. J. Med. Chem. vol. 36 pp. 3472-3480.

1994, "Stereospecific Synthesis of Peptidyl alpha-Keto Amides as Inhibitors of Calpain" Harbeson et al. J. Med. Chem. vol. 37 pp. 2918-2929.

Jan. 1, 1996 "Synthesis of Bestatin, A Potent Inhibitor of Leukotriene A4 Hydrolase, By an N3 Nucleophile Reaction to a Non-Protected Diol" Koshi Koseki et al. Bioscience Biotechnology Biochemistry, Japan Society for Bioscience, Biotechnology, and Agrochemistry vol. 60, No. 3 pp. 534-536.

Mar. 15, 2000 "Synthesis and Antifungal Activity of Rhodopeptin Analogues, 2. Modification of the West Amino Acid Moiety" Kiyoshi Nakayama et al. Organic Letters vol. 2, No. 7 pp. 977-980.

Apr. 20, 2000 "Passerini multicomponent reaction of protected alpha-aminoaldehydes as a tool for combinatorial syntheses of enzyme inhibitors" Luca Banfi et al. Chemical Communications vol. 11, pp. 985-986.

May 19, 1998 "An Alternative Synthesis of Peptidyl alpha-Keto-2-Oxazolines" Derek Dunn et al. Bioorganic & Medicinal Chemistry Letters, Pergamon, Elsevier Science vol. 8, No. 10 pp. 1273-1276.

Aug. 1, 1994 "Structure-Activity Relationships of HIV-1 PR Inhibitors Containing AHPBA" Mitsuya Sakurai et al. Biorganic & Medicinal Chemistry, Pergamon vol. 2, No. 8 pp. 807-825.

\* cited by examiner

EPOXYCARBOXAMIDE COMPOUND, AZIDE COMPOUND, AND AMINO ALCOHOL COMPOUND, AND PROCESS FOR PREPARING α-KETO AMIDE COMPOUND USING THEM

This is a divisional application of Ser. No. 10/331,702, now allowed, filed Dec. 30, 2002, which is in turn a continuation-in-part application of PCT/JP01/05668 filed on Jun. 29, 2001 claiming priorities of Japanese Patent Applications No. 2000-198089, No. 2000-198090 and No. 2000-198091 all of which were filed on Jun. 30, 2000, now abandoned. The subject matter of the aforementioned prior applications is hereby incorporated herein by reference.

FIELD OF THE INVENTION

The present invention relates to an epoxycarboxamide compound, an azide compound, and an amino alcohol compound, and a process for preparing an α-keto amide compound using them, and more particularly to an epoxycarboxamide compound, an azide compound, and an amino alcohol compound, which can be used as an intermediate product in the preparation of an α-keto amide compound having a protease inhibiting activity, and a process for preparing an α-keto amide compound using the above compounds.

BACKGROUND ART

It is known that a protease, which is a proteolytic enzyme, is responsible for the onset and progression of various diseases such as hypertension, thrombosis, pancreatitis, cancer, an Alzheimer disease, pulmonary emphysema, a nerve degeneration disease, an allergic disease, muscular dystrophy, a rheumatic disease, osteoporosis and a periodontal disease (Protein, NucleicAcid, and Enzyme, vol. 42, No. 14 (1997); and Experimental Medicine, vol. 17, No. 15 (1999)), and inhibitor substances of protease, namely, protease inhibitors are expected as a target of medicines.

An α-keto amide compound, which has been reported (Japanese Provisional Patent Publication No. 149166/1992; Japanese Provisional Patent Publication No. 211648/1992; Japanese PCT Provisional Patent Publication No. 504547/1994; WO9816512; J. Med. Chem., 39, 4089 (1996); and Exp. Opin. Ther. Patents., 8, 1707 (1998)) to have an inhibiting activity with respect to protease, especially serine protease (elastase, tryptase, trypsin, chymotrypsin, and prolyl endopeptidase) and cysteine protease (calpain, cathepsin B, and cathepsin L), is a compound expected to possibly have an inhibiting activity with respect to cathepsin K, which has recently been reported to be closely responsible for bone metabolism.

As a representative synthesis method for a protease inhibitor having an α-keto amide structure, (A) J. Med. Chem., 36, 3472 (1993) is known, and further, as a representative synthesis method for optically active substances thereof, (B) J. Med. Chem., 37, 2918 (1994) is known.

By the above (A) method, an α-keto amide compound which is a desired compound cannot be obtained in the form of an optically active substance. Further, the above (B) method has the following problems: (1) an optically active amino acid as a starting material is expensive; (2) since an amino acid is used as a starting material, only a limited substituent can be introduced into the oxirane ring as substituent $R^1$ (see general formula (I)); and (3) an α-hydroxy group in the reaction precursor cannot be stereoselectively controlled, and therefore a product is obtained in the form of a diastereomer mixture and satisfactory purification for the product is difficult. Thus, the above methods are not satisfactory as an industrial production process.

The present inventors have conducted extensive and intensive studies with a view toward solving the problems accompanying the prior art. As a result, they have found raw materials (an epoxycarboxamide compound, an azide compound, and an amino alcohol compound) for preparation of an α-keto amide compound, which are advantageous not only in that substituent $R^1$ is not restricted by the amino acid structure, but also in that an α-keto amide compound can be stereoselectively formed, and thus have completed the present invention.

DISCLOSURE OF THE INVENTION

Specifically, the epoxycarboxamide compound of the present invention is represented by the following formula (I):

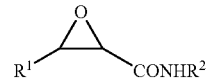

(I)

wherein $R^1$ represents a substituted or unsubstituted, straight, branched or cyclic alkyl group, a substituted or unsubstituted, straight, branched or cyclic alkenyl group, a substituted or unsubstituted aromatic hydrocarbon group or a substituted or unsubstituted heterocyclic group, where the substituent for the alkyl group, alkenyl group, aromatic hydrocarbon group or heterocyclic group is a substituted or unsubstituted aromatic hydrocarbon group, a substituted or unsubstituted heterocyclic group, a substituted or unsubstituted alkoxy group, a substituted or unsubstituted alkylthio group, a substituted or unsubstituted aryloxy group or a substituted or unsubstituted arylthio group; and $R^2$ represents a substituted or unsubstituted, straight, branched or cyclic alkyl group, a substituted or unsubstituted, straight, branched or cyclic alkenyl group, a substituted or unsubstituted aromatic hydrocarbon group or a substituted or unsubstituted heterocyclic group, where the substituent for the alkyl group, alkenyl group, aromatic hydrocarbon group or heterocyclic group is a hydroxy group, an oxo group, a halogen atom, a substituted or unsubstituted, straight, branched or cyclic alkenyl group having 2 to 6 carbon atoms, a substituted or unsubstituted aromatic hydrocarbon group, a substituted or unsubstituted heterocyclic group, a nitro group, a substituted or unsubstituted amino group, a substituted or unsubstituted sulfonyl group, a substituted or unsubstituted alkoxy group, a substituted or unsubstituted alkylthio group, a substituted or unsubstituted aryloxy group, a substituted or unsubstituted arylthio group, an acyl group, a substituted or unsubstituted alkoxycarbonyl group, a substituted carbamoyl group, a substituted sulfonamide group, a substituted amide group, a mercapto group, a cyano group or a methylenedioxy group.

Also, the azide compound of the present invention is represented by the following formula (VI):

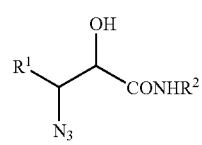

(VI)

wherein $R^1$ and $R^2$ have the same meanings as defined above.

Moreover, the amino alcohol compound of the present invention is represented by the following formula (IX):

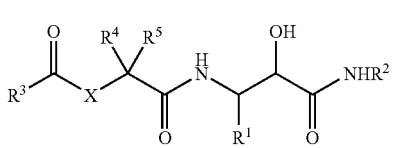 (IX)

wherein $R^1$ and $R^2$ have the same meanings as defined above, $R^3$ represents a substituted or unsubstituted, straight, branched or cyclic alkyl group, a substituted or unsubstituted, straight, branched or cyclic alkenyl group, a substituted or unsubstituted aromatic hydrocarbon group, a substituted or unsubstituted heterocyclic group, $R^6$—O— or $R^7$—N($R^8$)—, where $R^6$ represents a substituted or unsubstituted, straight, branched or cyclic alkyl group, a substituted or unsubstituted, straight, branched or cyclic alkenyl group, a substituted or unsubstituted aromatic hydrocarbon group or a substituted or unsubstituted heterocyclic group, $R^7$ and $R^8$ may be the same or different from each other, and each represents a hydrogen atom, a substituted or unsubstituted, straight, branched or cyclic alkyl group, a substituted or unsubstituted, straight, branched or cyclic alkenyl group, a substituted or unsubstituted aromatic hydrocarbon group or a substituted or unsubstituted heterocyclic group, where the substituent for the alkyl group, alkenyl group, aromatic hydrocarbon group or heterocyclic group is a hydroxy group, an oxo group, a halogen atom, a substituted or unsubstituted, straight, branched or cyclic alkenyl group having 2 to 6 carbon atoms, a substituted or unsubstituted aromatic hydrocarbon group, a substituted or unsubstituted heterocyclic group, a nitro group, a substituted or unsubstituted amino group, a substituted or unsubstituted sulfonyl group, a substituted or unsubstituted alkoxy group, a substituted or unsubstituted alkylthio group, a substituted or unsubstituted aryloxy group, a substituted or unsubstituted arylthio group, an acyl group, a substituted or unsubstituted alkoxycarbonyl group, a substituted carbamoyl group, a substituted sulfonamide group, a substituted amide group, a mercapto group, a cyano group or a methylenedioxy group; $R^4$ and $R^5$ represent the same groups as $R^7$ and $R^8$, respectively, and $R^4$ and $R^5$ optionally form a ring together with the carbon atom through which $R^4$ and $R^5$ are bonded; and X represents —O— or —N($R^9$)— where $R^9$ represents a hydrogen atom or a substituted or unsubstituted, straight, branched or cyclic alkyl group, and X optionally forms a ring together with $R^4$ or $R^5$.

Further, the present invention provides a process for preparing an α-keto amide compound represented by the following formula (X):

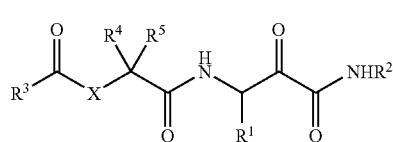 (X)

wherein $R^1$ to $R^5$ and X have the same meanings as defined above, wherein the process comprises oxidizing an aminoalcohol compound represented by the following formula (IX):

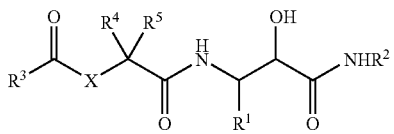 (IX)

wherein $R^1$ to $R^5$ and X have the same meanings as defined above.

Further, the present invention provides a process for preparing an α-keto amide compound represented by the following formula (X):

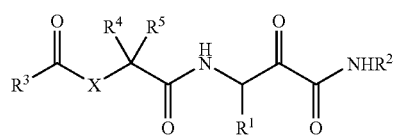 (X)

wherein $R^1$ to $R^5$ and X have the same meanings as defined above, wherein the process comprises: reducing an azide compound represented by the following formula (VI):

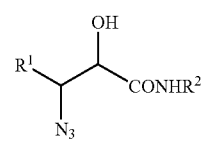 (VI)

wherein $R^1$ and $R^2$ have the same meanings as defined above, to obtain an amine compound represented by the following formula (VII):

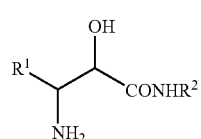 (VII)

wherein $R^1$ and $R^2$ have the same meanings as defined above; condensing the obtained amine compound with a carboxylic acid compound represented by the following formula (VIII):

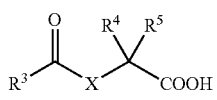 (VIII)

wherein $R^3$ to $R^5$ and X have the same meanings as defined above, to obtain an amino alcohol compound represented by the following formula (IX):

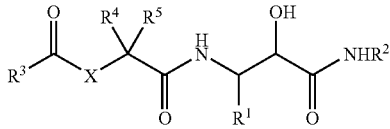

wherein $R^1$ to $R^5$ and X have the same meanings as defined above;
and then oxidizing the obtained amino alcohol compound.

Further, the present invention provides a process for preparing an α-keto amide compound represented by the following formula (X):

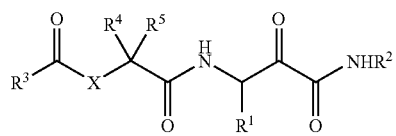

wherein $R^1$ to $R^5$ and X have the same meanings as defined above,
wherein the process comprises: subjecting an epoxycarboxamide compound represented by the following formula (I):

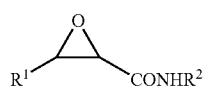

wherein $R^1$ and $R^2$ have the same meanings as defined above, to epoxy group ring-opening in the presence of a ring-opening agent to obtain an azide compound represented by the following formula (VI):

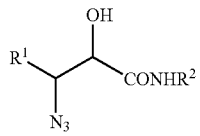

wherein $R^1$ and $R^2$ have the same meanings as defined above; then reducing the obtained azide compound to obtain an amine compound represented by the following formula (VII):

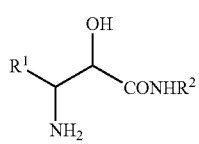

wherein $R^1$ and $R^2$ have the same meanings as defined above; condensing the obtained amine compound with a carboxylic acid compound represented by the following formula (VIII):

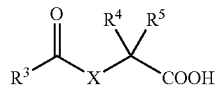

wherein $R^3$ to $R^5$ and X have the same meanings as defined above,
to obtain an amino alcohol compound represented by the following formula (IX):

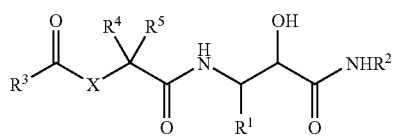

wherein $R^1$ to $R^5$ and X have the same meanings as defined above;
and then oxidizing the obtained amino alcohol compound.

BEST MODE FOR CARRYING OUT THE INVENTION

Hereinbelow, the present invention will be described in more detail.

The compounds of the present invention are represented by the above-mentioned formulae (I), (VI) and (IX). The compound of the formula (IX) has four optical isomers represented by the following formulae (IXa) to (IXd), and all of these isomers are included in the present invention.

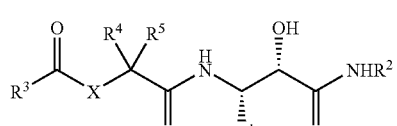

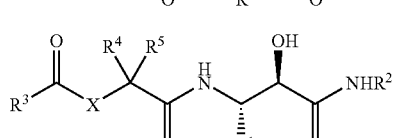

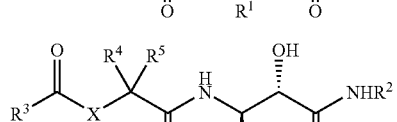

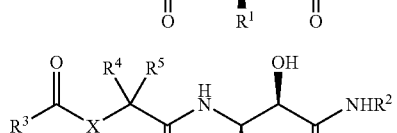

wherein $R^1$ to $R^5$ and X have the same meanings as defined above.

In each of the above-mentioned formulae (I) and (IV) to (IX), alkyl groups in the substituted or unsubstituted alkyl groups of $R^1$ to $R^9$ may be individually any of straight, branched or cyclic alkyl groups having 1 to 12 carbon atoms, and there may be mentioned, for example, a methyl group, an ethyl group, a n-propyl group, a 1-methylethyl group, a cyclopropyl group, a n-butyl group, a t-butyl group, a 2-methylpropyl group, a 1-methylpropyl group, a 1,1-dimethylethyl group, a cyclobutyl group, a n-pentyl group, a 3-methylbutyl group, a cyclopentyl group, a 2,2-dimethylpropyl group, a 1-methylcyclobutyl group, a cyclobutylmethyl group, a n-hexyl group, a 4-methylpentyl group, a cyclohexyl group, a 1-methylcyclopentyl group, a cyclopentylmethyl group, a (1-methylcyclobutyl)methyl group, a n-heptyl group, a 5-methylhexyl group, a 4,4-dimethylpentyl group, a cycloheptyl group, a cyclohexylmethyl group, a (1-methylcyclopentyl) methyl group, a n-octyl group, a 6-methylheptyl group, a 5,5-dimethylhexyl group, a (1-methylcyclohexyl)methyl group, a n-nonyl group, a 7-methyloctyl group, a 6,6-dimethylheptyl group, a n-decyl group, an 8-methylnonyl group, a 7,7-dimethyloctyl group, a n-undecyl group, a 9-methyldecyl group, an 8,8-dimethylnonyl group, a n-dodecyl group, a 10-methylundecyl group and a 9,9-dimethyldecyl group.

Also, the alkenyl groups in the substituted or unsubstituted alkenyl groups of $R^1$ to $R^8$ may be any of straight, branched or cyclic alkenyl groups having 2 to 6 carbon atoms, and there may be mentioned, for example, a 1-methyl-1-propenyl group, a 1-methyl-2-propenyl group, a 2-methyl-2-propenyl group, an ethenyl group, a 1-methylethenyl group, a 1-propenyl group, a 2-propenyl group, a 1-butenyl group, a 2-butenyl group, a 2-pentenyl group, a 1-pentenyl group, a 1,3-butanedienyl group, a 1-hexenyl group, a 2-hexenyl group, a 1,3-pentadienyl group and a 1,3-hexadienyl group. Examples of the substituents for the alkenyl group include substituted or unsubstituted aromatic hydrocarbon groups and substituted or unsubstituted heterocyclic groups mentioned below.

The substituted or unsubstituted aromatic hydrocarbon groups of $R^1$ to $R^8$ are individually a monocyclic or polycyclic aromatic hydrocarbon group which optionally further has at least one substituent in its ring. Examples of such unsubstituted aromatic hydrocarbon groups include a phenyl group, a 1-naphthyl group and a 2-naphthyl group.

The substituted or unsubstituted heterocyclic groups of $R^1$ to $R^8$ are individually a 5-membered or 6-membered ring group having at least one heteroatom such as a nitrogen atom, a sulfur atom and an oxygen atom, as an atom constituting the ring, and may be condensed with a benzene ring, and there may be mentioned, for example, a 2-pyridyl group, a 2-furyl group, a 2-thienyl group, a 2-indolyl group, a 2-quinolyl group, a 3-isoquinolyl group, a 2-benzofuranyl group, a 2-benzothienyl group, a 2-imidazolyl group, a 2-benzimidazolyl group, a 2-thiazolyl group, a 2-oxazolyl group, a 2-pyrazolyl group, a 2-pyrrimidyl group, a 2-pyrrimidinyl group, a 2-dioxanyl group, a 2-thiazolidinyl group, a 2-imidazolidinyl group, a 2-oxo-tetrahydrofuran-3-yl group, a 2-benzothiazolyl group, a 2-quinazoline group, a hexahydro-2-azepine-3-yl group, a morpholino group, a thiamorpholino group, a pyrrolidino group, a piperidino group, a piperazino group, a perhydro-4-azepine-1-yl group, and a perhydro-4-azaazepine-1-yl group. These heterocyclic groups may individually have at least one substituent in their heterocyclic rings, and examples of substituents include an acetyl group, a methoxycarbonyl group, an ethoxycarbonyl group, a 2-methyl-2-propyloxycarbonyl group, a methylsulfonyl group, a methoxy group and a benzoyl group.

Examples of the substituents for the above alkyl group, alkenyl group, aromatic hydrocarbon group or heterocyclic group include a hydroxy group, an oxo group, a halogen atom, a substituted or unsubstituted, straight, branched or cyclic alkenyl group having 2 to 6 carbon atoms, a substituted or unsubstituted aromatic hydrocarbon group, a substituted or unsubstituted heterocyclic group, a nitro group, a substituted or unsubstituted amino group, a substituted or unsubstituted sulfonyl group, a substituted or unsubstituted alkoxy group, a substituted or unsubstituted alkylthio group, a substituted or unsubstituted aryloxy group, a substituted or unsubstituted arylthio group, an acyl group, a substituted or unsubstituted alkoxycarbonyl group, a substituted carbamoyl group, a substituted sulfonamide group, a substituted amide group, a mercapto group, a cyano group and a methylenedioxy group.

Here, as examples of the alkenyl groups which are mentioned above as examples of the substituents for the alkyl groups of $R^1$ to $R^9$ or alkenyl groups, aromatic hydrocarbon groups or heterocyclic groups of $R^1$ to $R^8$, there can be mentioned the same groups as the above-described alkenyl groups.

Also, as examples of the substituted or unsubstituted aromatic hydrocarbon groups which are substituents for the alkyl groups of $R^1$ to $R^9$ or the alkenyl groups, aromatic hydrocarbon groups or heterocyclic groups of $R^1$ to $R^8$, there can be mentioned the same groups as the above-described aromatic hydrocarbon groups.

As examples of the substituted or unsubstituted heterocyclic groups which are substituents for the alkyl groups of $R^1$ to $R^9$ or the alkenyl groups, aromatic hydrocarbon groups or heterocyclic groups of $R^1$ to $R^8$, there can be mentioned the same groups as the above-described heterocyclic groups.

The substituted amino groups which are substituents for the alkyl groups of $R^1$ to $R^9$ or the alkenyl groups, aromatic hydrocarbon groups or heterocyclic groups of $R^1$ to $R^8$ are secondary amino groups or tertiary amino groups substituted with various substituents, and, as examples of these substituents, there can be mentioned the same groups as the above-described substituted or unsubstituted alkyl groups, substituted or unsubstituted alkenyl groups, substituted or unsubstituted aromatic hydrocarbon groups and substituted or unsubstituted heterocyclic groups.

Examples of the substituted sulfonyl groups which are the substituents for the alkyl groups of $R^1$ to $R^9$ or the alkenyl groups, aromatic hydrocarbon groups or heterocyclic groups of $R^1$ to $R^8$ include a methylsulfonyl group, a n-butylsulfonyl group, a 2,2-dimethylethylsulfonyl group, a cyclohexylsulfonyl group, a phenylsulfonyl group, a 4-methylphenylsulfonyl group, a 4-fluorophenylsulfonyl group, a 4-chlorophenylsulfonyl group, a 4-nitrophenylsulfonyl group, a 2-naphthylsulfonyl group, a 3,4-dimethoxyphenylsulfonyl group, a 3,4-methylenedioxy-phenylsulfonyl group, a 2-pyridylsulfonyl group, a furyl-sulfonyl group, a 2-thienylsulfonyl group, a 2-quinolylsulfonyl group, a 3-isoquinolylsulfonyl group, a phenylmethylsulfonyl group, a 4-fluorophenylmethylsulfonyl group, a 4-chlorophenylmethylsulfonyl group, a 4-nitrophenylmethylsulfonyl group, a 2-naphthylmethylsulfonyl group, a 3,4-dimethoxy-phenylmethylsulfonyl group and a 3,4-methylenedioxyphenyl-methylsulfonyl group.

The alkoxy groups which are substituents for the alkyl groups of $R^1$ to $R^9$ or the alkenyl groups, aromatic hydrocarbon groups or heterocyclic groups of $R^1$ to $R^8$ are alkyl-substituted oxy groups having an alkyl portion comprised of the above-mentioned alkyl group having 1 to 6 carbon atoms, and examples include a methoxy group, an ethoxy group, a n-propoxy group, a 1-methylethyloxy group, a n-butoxy group, a 2-methylpropyloxy group, a 1-methylpropyloxy group, a 2-methyl-2-propyloxy group, a 2,2-dimethylethyloxy group, a n-pentyloxy group, a 3-methylbutyloxy group, a n-hexyloxy group, a 4-methylpentyloxy group and a cyclohexyloxy group. As examples of substituents for these alkoxy groups, there can be mentioned the same groups as the above-described substituents for the alkenyl groups.

The alkylthio groups which are substituents for the alkyl groups of $R^1$ to $R^9$ or the alkenyl groups, aromatic hydrocarbon groups or heterocyclic groups of $R^1$ to $R^8$ are alkyl-substituted thio groups having an alkyl portion comprised of the above-mentioned alkyl group having 1 to 6 carbon atoms, and examples include a methylthio group, an ethylthio group, a n-propylthio group, a 1-methylethylthio group, a n-butylthio group, a 2-methylpropylthio group, a 1-methylpropylthio group, a 2-methyl-2-propylthio group, a 2,2-dimethylethylthio group, a n-pentylthio group, a 3-methylbutylthio group, a n-hexylthio group, a 4-methylpentylthio group and a cyclohexylthio group. As examples of substituents for these alkylthio groups, there can be mentioned the same groups as the above-described substituents for the alkenyl groups.

Examples of the substituted or unsubstituted aryloxy groups which are substituents for the alkyl groups of $R^1$ to $R^9$ or the alkenyl groups, aromatic hydrocarbon groups or heterocyclic groups of $R^1$ to $R^8$ include a phenyloxy group, a 4-methylphenyloxy group, a 4-fluorophenyloxy group, a 4-chlorophenyloxy group, a 4-nitrophenyloxy group, a 2-naphthyloxy group, a 3,4-dimethoxyphenyloxy group, a 3,4-methylene-dioxyphenyloxygroup, a2-pyridyloxygroup, a2-furyloxygroup, a2-thienyloxygroup, a2-quinolyloxygroup, a3-isoquinolyloxy group, a 4-nitrophenylmethyloxy group, a 2-naphthylmethyloxy group, a 3,4-dimethoxyphenyloxy group and a 3,4-methylene-dioxyphenylmethyloxy group.

Examples of the substituted or unsubstituted arylthio groups which are substituents for alkyl groups of $R^1$ to $R^9$ or the alkenyl groups, aromatic hydrocarbon groups or heterocyclic groups of $R^1$ to $R^8$ include a phenylthio group, a 4-methylphenylthio group, a 4-fluorophenylthio group, a 4-chlorophenylthio group, a 4-nitrophenylthio group, a 2-naphthylthio group, a 3,4-dimethoxyphenylthio group, a 3,4-methylenedioxyphenylthio group, a 2-pyridylthio group, a 2-furylthio group, a 2-thienylthio group, a 2-quinolylthio group, a 3-isoquinolylthio group, a phenylmethylthio group, a 4-fluorophenylmethylthio group, a 4-chlorophenylmethylthio group, a 4-nitrophenylmethylthio group, a 2-naphthylmethylthio group, a 3,4-di-methoxyphenylmethylthio group and a 3,4-methylenedioxyphenylmethylthio group.

Examples of the acyl group which are substituents for the alkyl groups of $R^1$ to $R^9$ or the alkenyl groups, aromatic hydrocarbon groups or heterocyclic groups of $R^1$ to $R^8$ include an acetyl group, a propanoyl group, a butanoyl group, a pentanoyl group, a hexanoyl group, a cyclohexanecarbonyl group, a benzoyl group, a piperonyloyl group, a naphthoyl group, a pivaloyl group, a phenylacetyl group, a pyridinecarbonyl group and a furancarbonyl group.

Examples of the substituted or unsubstituted alkoxycarbonyl groups which are substituents for the alkyl groups of $R^1$ to $R^9$ or the alkenyl groups, aromatic hydrocarbon groups or heterocyclic groups of $R^1$ to $R^8$ include a methoxycarbonyl group, an ethoxycarbonyl group, a n-propoxycarbonyl group, a n-butyoxycarbonyl group, a 2,2-dimethylethyloxycarbonyl group, a cyclohexyloxycarbonyl group and a phenylmethyloxycarbonyl group.

The substituted carbamoyl groups which are the substituents for alkyl groups of $R^1$ to $R^9$ or the alkenyl groups, aromatic hydrocarbon groups or heterocyclic groups of $R^1$ to $R^8$ are groups represented by $R^{10}$—NHCO— in which a substituent is bonded to the nitrogen atom in the carbamoyl group. As examples of the substituents $R^{10}$ bonded to the nitrogen atom, there can be mentioned the above-described substituted or unsubstituted alkyl groups, substituted or unsubstituted alkenyl groups, substituted or unsubstituted aromatic hydrocarbon groups, substituted or unsubstituted heterocyclic groups and substituted or unsubstituted amino groups. Specific examples of the substituted carbamoyl groups include an N-methylcarbamoyl group, an N,N-dimethylcarbamoyl group, an N-butylcarbamoyl group, an N,N-dibutylcarbamoyl group, an N-(2,2-dimethyl-ethyl)carbamoyl group, an N-cyclohexylcarbamoyl group, an N-phenylcarbamoyl group, an N-(4-methylphenyl) carbamoyl group, an N-(4-fluorophenyl)carbamoyl group, an N-(4-chloro-phenyl) carbamoyl group, an N-(4-nitrophenyl) carbamoyl group, an N,N-diphenylcarbamoyl group, an N-naphthylcarbamoyl group, an N-(3,4-dimethoxyphenyl) carbamoyl group, an N-(3,4-methylenedioxyphenyl)carbamoyl group, an N-methyl-N-phenyl-carbamoyl group, an N-methyl-N-naphthylcarbamoyl group, an N-(2-pyridyl) carbamoyl group, an N-(2-furyl) carbamoyl group, an N-(2-thienyl)carbamoyl group, an N-(2-quinolyl)carbamoyl group, an N-(3-isoquinolyl)carbamoyl group, an N-(phenylmethyl) carbamoyl group, an N-(4-fluorophenylmethyl) carbamoyl group, an N-(4-chlorophenylmethyl)carbamoyl group, an N-(4-nitrophenylmethyl)carbamoyl group, an N-(naphthyl-methyl)carbamoyl group, an N-(3,4-dimethoxyphenylmethyl)-carbamoyl group and an N-(3,4-methylenedioxyphenylmethyl)-carbamoyl group.

The substituted sulfonamide groups which are the substituents for the alkyl groups of $R^1$ to $R^9$ or the alkenyl groups, aromatic hydrocarbon groups or heterocyclic groups of $R^1$ to $R^8$ are groups represented by $R^{11}$—$SO_2NH$— in which a substituent is bonded to the sulfur atom in the sulfonamide group, and examples of the substituents $R^{11}$ bonded to the sulfur atom include the above-described substituted or unsubstituted alkyl groups, substituted or unsubstituted alkenyl groups, substituted or unsubstituted aromatic hydrocarbon groups, substituted or unsubstituted heterocyclic groups and substituted or unsubstituted amino groups.

The substituted amide groups which are the substituents for the alkyl groups of $R^1$ to $R^9$ or the alkenyl groups, aromatic hydrocarbon groups or heterocyclic groups of $R^1$ to $R^8$ are groups represented by $R^{12}$—CONH— in which a substituent is bonded to the carbon atom in the amide group, and examples of the substituents $R^{12}$ bonded to the carbon atom include a phenoxy group, a 1-naphthyloxy group, a 2-naphthyloxy group, the above-described substituted or unsubstituted alkyl groups, substituted or unsubstituted alkenyl groups, substituted or unsubstituted aromatic hydrocarbon groups, substituted or unsubstituted heterocyclic groups, substituted or unsubstituted amino groups and substituted or unsubstituted alkoxy groups.

In each of the formulae (I) and (IV) to (IX) above, examples of the substituted aromatic hydrocarbon groups of $R^1$ to $R^8$ include a 4-methylphenyl group, a 3,4-dimethylphenyl group, a 4-methoxyphenyl group, a 2,3-dimethoxyphenyl group, a 3,4-dimethoxyphenyl group, a 3,5-dimethoxyphenyl group, a 2,3-methylenedioxyphenyl group, a 3,4-methylenedioxyphenyl group, a 4-nitrophenyl group, a 3,4-dinitrophenyl group, a 4-chlorophenyl group, a 3,4-dichlorophenyl group, a 4-bromophenyl group, a 3,4-dibromophenyl group, a 4-iodophenyl group, a 4-fluorophenyl group, a 2,3-difluorophenyl group, a 3,4-difluorophenyl group, a 3,5-difluorophenyl group, a 4-trifluoromethylphenyl group, a 3-phenoxyphenyl group, a 4-phenoxyphenyl group, a 4-(1-naphthoxy)phenyl group and a 4-acetaminophenyl group.

The ring formed from $R^4$ and $R^5$ together with the carbon atom through which they are bonded is a saturated cyclic alkyl group having 5 to 7 carbon atoms or a saturated heterocyclic group containing a heteroatom and having 3 to 6 carbon atoms. Examples of the saturated cyclic alkyl groups having 5 to 7 carbon atoms include groups derived individually from cyclopentane, cyclohexane and cycloheptane. On the other hand, examples of the saturated heterocyclic groups containing a heteroatom and having 3 to 6 carbon atoms include groups derived individually from pyrrolidine, piperidine, piperazine, morpholine, perhydroazepine, oxolane, oxane, oxepane, thiolane, thiane and thiepane, and examples of the heteroatoms include an oxygen atom, a sulfur atom and a nitrogen atom. The saturated heterocyclic groups containing a heteroatom and having 3 to 6 carbon atoms can be fused with a benzene ring. Each of the saturated cyclic alkyl groups having 5 to 7 carbon atoms and the saturated heterocyclic groups containing a heteroatom and having 3 to 6 carbon atoms may have a substituent, and, as examples of the substituents, there can be mentioned the same groups as the above-described hydroxy group, halogen atoms, substituted or unsubstituted alkyl groups, substituted or unsubstituted aromatic hydrocarbon groups including a phenyl group, a methylphenyl group and a naphthyl group, substituted or unsubstituted heterocyclic groups including a thienyl group, a furyl group and a pyridyl group, nitro group, substituted or unsubstituted amino groups, substituted or unsubstituted sulfonyl groups, substituted or unsubstituted alkoxy groups, substituted or unsubstituted alkylthio groups, substituted or unsubstituted aryloxy groups, substituted or unsubstituted arylthio groups, acyl group, substituted or unsubstituted alkoxycarbonyl groups, substituted carbonyl groups, mercapto group and cyano group.

The ring formed from $N(R^9)$ and $R^4$ or $R^5$ together with the carbon atom through which they are bonded is a saturated heterocyclic group containing a nitrogen atom and having 3 to 6 carbon atoms. Examples of the saturated heterocyclic groups containing a nitrogen atom and having 3 to 6 carbon atoms include groups derived individually from pyrrolidine, piperidine, piperazine, morpholine and perhydroazepine, and these groups can be fused with a benzene ring. These saturated heterocyclic groups may have a substituent, and, as examples of substituents, there can be mentioned the same groups as the above-described hydroxy group, halogenatoms, substituted or unsubstituted alkyl groups, substituted or unsubstituted aromatic hydrocarbon groups including a phenyl group, a methylphenyl group and a naphthyl group, substituted or unsubstituted heterocyclic groups including a thienyl group, a furyl group and a pyridyl group, nitro group, substituted or unsubstituted amino groups, substituted or unsubstituted sulfonyl groups, substituted or unsubstituted alkoxy groups, substituted or unsubstituted alkylthio groups, substituted or unsubstituted aryloxy groups, substituted or unsubstituted arylthio groups, acyl group, substituted or unsubstituted alkoxycarbonyl groups, substituted carbonyl groups, mercapto group and cyano group.

In each of the compounds represented, respectively, by the formulae (I) and (VI) above, it is preferred that $R^1$ represents a substituted or unsubstituted, straight, branched or cyclic alkyl group, and that a substituent for the alkyl group is a substituted or unsubstituted aromatic hydrocarbon group, a substituted or unsubstituted heterocyclic group, a substituted or unsubstituted alkoxy group, a substituted or unsubstituted alkylthio group, a substituted or unsubstituted aryloxy group or a substituted or unsubstituted arylthio group; and it is preferred that $R^2$ represents a substituted or unsubstituted, straight, branched or cyclic alkyl group, and that a substituent for the alkyl group is a hydroxy group, an oxo group, a halogen atom, a substituted or unsubstituted, straight, branched or cyclic alkenyl group having 2 to 6 carbon atoms, a substituted or unsubstituted aromatic hydrocarbon group, a substituted or unsubstituted heterocyclic group, a nitro group, a substituted or unsubstituted amino group, a substituted or unsubstituted sulfonyl group, a substituted or unsubstituted alkoxy group, a substituted or unsubstituted alkylthio group, a substituted or unsubstituted aryloxy group, a substituted or unsubstituted arylthio group, an acyl group, a substituted or unsubstituted alkoxycarbonyl group, a substituted carbamoyl group, a substituted sulfonamide group, a substituted amide group, a mercapto group, a cyano group or a methylenedioxy group.

Especially, it is preferred that $R^2$ in the formula (I) is one of the above, straight, branched or cyclic alkyl groups having 1 to 12 carbon atoms, optionally having at least one substituent selected from the group consisting of a hydroxy group, an oxo group, a halogen atom, a substituted or unsubstituted, straight, branched or cyclic alkenyl group having 2 to 6 carbon atoms, a substituted or unsubstituted heterocyclic group, a nitro group, a substituted or unsubstituted amino group, a substituted or unsubstituted sulfonyl group, a substituted or unsubstituted alkoxy group, a substituted or unsubstituted alkylthio group, a substituted or unsubstituted aryloxy group, a substituted or unsubstituted arylthio group, an acyl group, a substituted or unsubstituted alkoxycarbonyl group, a substituted carbamoyl group, a substituted sulfonamide group, a substituted amide group, a mercapto group and a cyano group mentioned above and $R^1$ in the formula (VI) is one of the above, straight, branched or cyclic alkyl groups having 1 to 6 carbon atoms, optionally having at least one substituent selected from the group consisting of a substituted or unsubstituted aromatic hydrocarbon group, a substituted or unsubstituted heterocyclic group, a substituted or unsubstituted alkoxy group, a substituted or unsubstituted alkylthio group, a substituted or unsubstituted aryloxy group or a substituted or unsubstituted arylthio group mentioned above.

More preferred substituents are shown below. $R^1$ may be an unsubstituted alkyl group, preferably a n-butyl group. $R^2$ may be a substituted or unsubstituted cyclic alkyl group, more specifically, a substituted or unsubstituted cyclohexyl group, preferably a hydroxycyclohexyl group; an unsubstituted alkyl group, preferably a n-butyl group; a substituted alkyl group, preferably a methoxyoxophenylpropyl group; or a substituted phenyl group, preferably a methylenedioxyphenyl group. $R^3$ may be a 5-membered or 6-membered heterocyclic group, preferably a morpholino group; an unsubstituted alkyl group, preferably a methyl group; or a phenylalkoxy group, preferably a phenylmethoxy group. One of $R^4$ and $R^5$ may be a hydrogen atom and another may be an unsubstituted alkyl group, preferably, one of $R^4$ and $R^5$ is a hydrogen atom and another is a t-butyl group; or one of $R^4$ and $R^5$ may be a hydrogen atom and another may be a phenylalkyl group, preferably, one of $R^4$ and $R^5$ is a hydrogen atom and another is a benzyl group. Alternatively, $R^4$ and $R^5$ may form a saturated cyclic alkyl group having 5 to 7 carbon atoms, preferably a saturated cyclic alkyl group having 6 carbon atoms, together with the carbon atom through which $R^4$ and $R^5$ are bonded. X may be —NH— or —O—, and, when X is —$N(R^9)$—, X and $R^4$ or $R^5$ together form a pyrrolidino group.

More specifically, examples of the compounds (I) include (2S-trans)-N-[(1S,2S)-2-hydroxycyclohexane-1-yl]-3-butyl-oxiranecarboxamide, (2S-trans)-N-[(3,4-methylenedioxy)-phenyl]-3-butyloxiranecarboxamide, (2S-trans)-N-butyl-3-butyloxiranecarboxamide and (2S-trans)-N-[(2S)-1-methoxy-1-oxo-3-phenyl-2-propyl]-3-butyloxiranecarboxamide.

Examples of the compounds (VI) include (2S,3S)-N-[(1S,2S)-2-hydroxycyclohexane-1-yl]-3-azido-2-hydroxyheptanamide, (2S,3S)-N-[(3,4-methylenedioxy)phenyl]-3-azido-2-hydroxyheptanamide, (2S,3S)-N-butyl-3-azido-2-hydroxyheptanamide and (2S,3S)-N-[(2S)-1-methoxy-1-oxo-3-phenyl-2-propyl]-3-azido-2-hydroxyheptanamide.

Examples of the compounds (IX) include N-[(2S,3S)-2-hydroxy-1-[N-[(1S,2S)-2-hydroxycyclohexane-1-yl]amino]-1-oxo-3-heptyl]-1-[N-(morpholine-4-carbonyl)amino]cyclo-hexanecarboxamide, N-[(2S,3S)-2-hydroxy-1-[N-[(3,4-methyl-enedioxy)phenyl]amino]-1-oxo-3-heptyl]-1-[N-(morpholine-4-carbonyl)amino]cyclohexanecarboxamide, N-[(2S,3S)-2-hydroxy-1-[N-(butyl)-amino]-1-oxo-3-heptyl]-1-[N-(morpho-line-4-carbonyl)amino]cyclohexanecarboxamide, N-[(2S,3S)-2-hydroxy-1-[N-[(2S)-1-methoxy-1-oxo-3-phenyl-2-propyl]-amino]-1-oxo-3-heptyl]-1-[N-(morpholine-4-carbonyl)amino]-cyclohexanecarboxamide, (2S)-N-[(2S,3S)-2-hydroxy-1-[N-[(1S,2S)-2-hydroxycyclohexane-1-yl]amino]-1-oxo-3-heptyl]-2-(2-methylcarbonyloxy)-3-phenylpropylamide, (2S)-N-[(2S,3S)-2-hydroxy-1-[N-[(1S,2S)-2-hydroxycyclohexane-1-yl]amino]-1-oxo-3-heptyl]-4-methyl-2-[N-(phenylmethoxy-carbonyl)amino]pentanamide and (2S)-N-[(2S,3S)-2-hydroxy-1-[N-[(1S,2S)-2-hydroxy-cyclohexane-1-yl]amino]-1-oxo-3-heptyl]-1-(phenyl-methoxycarbonyl)pyrrolidine-2-carboxamide.

An epoxycarboxamide compound represented by the above-mentioned formula (I) can be stereoselectively prepared in accordance with the following scheme.

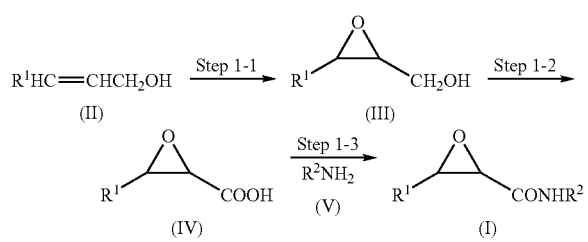

wherein $R^1$ and $R^2$ are, respectively, the same as $R^1$ and $R^2$ in the above-mentioned formula (I).

Incidentally, the compound of the formula (I) has four optical isomers represented by the formulae (Ia) to (Id) mentioned below, and all of these isomers are included in the present invention.

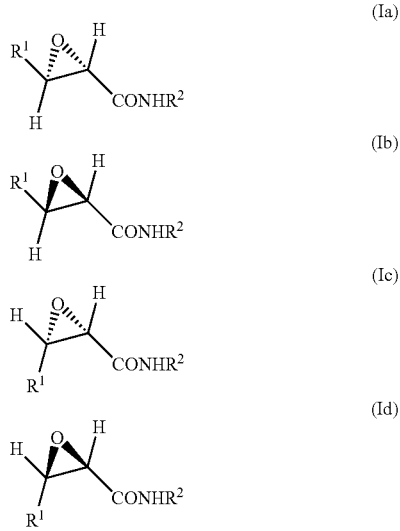

(Step 1-1)

This is a step of oxidizing an unsaturated alcohol compound represented by the above-mentioned formula (II) to prepare an epoxy alcohol compound represented by the above-mentioned formula (III).

As an oxidation reaction to be used in this step, there may be mentioned, for example, a Sharpless oxidation method. As an oxidizing agent, t-butyl hydroperoxide, cumene hydroperoxide or trityl hydroperoxide can be used, and, as a catalyst, titanium tetraisopropoxide can be used. As an asymmetric agent, there may be used, for example, a tartaric acid ester which is an optically active substance such as diisopropyl tartrate, diethyl tartrate and dimethyl tartrate. It is desired that the reaction is effected in an inert solvent, and there may be used, for example, a halogenated hydrocarbon such as dichloromethane, chloroform and dichloroethane or an aromatic hydrocarbon such as benzene, toluene and xylene. The amount of the oxidizing agent used is generally an equimolar amount to a 20-fold molar amount, preferably an equimolar amount to a 10-fold molar amount, relative to the mole of the compound (II). The amount of the catalyst used is generally a 0.001-fold molar amount to a 10-fold molar amount, preferably a 0.05-fold molar amount to an equimolar amount, relative to the mole of the compound (II). The amount of the asymmetric agent used is generally an equimolar amount to a 10-fold molar amount, preferably an equimolar amount to a 2-fold molar amount, relative to the mole of the catalyst. Incidentally, the reaction can be conducted in such a manner that the temperature is gradually elevated from −40° C. to room temperature.

In this step, according to the stereostructures of the unsaturated alcohol compound (II) and the asymmetric agent, four types of epoxy alcohol compounds (III) shown in Table 1 below can be stereoselectively prepared.

TABLE 1

| Alcohol compound | Asymmetric agent | Epoxy alcohol compound |
|---|---|---|
| | D-(−)tartarate | |
|  | L-(+)-tartarate | |
| | D-(−)-tartarate | |
|  | L-(+)-tartarate | |

In the table, $R^1$ is the same as $R^1$ in the above-mentioned formula (I).

(Step 1-2)

This step is a step of oxidizing the epoxy alcohol compound represented by the above-mentioned formula (III) while maintaining the stereostructure to prepare an epoxycarboxylic acid compound represented by the above-mentioned formula (IV).

In this step, in the reaction of oxidizing the epoxy alcohol compound represented by the above-mentioned formula (III), as an oxidizing agent, an oxidization reagent such as sodium periodate and periodic acid can be used, and, as a catalyst, ruthenium chloride can be used. As a reaction solvent, a mixed solvent of acetonitrile/carbon tetrachloride/water is desirably used, and the reaction temperature can be −10° C. to 30° C.

With respect to the amount of the oxidizing agent used, there is no particular limitation, and the amount can be selected from the wide range. And it is generally an equimolar amount to a 100-fold molar amount, preferably an equimolar amount to a 10-fold molar amount, relative to the mole of the compound (III).

(Step 1-3)

This step is a step of condensing the epoxycarboxylic acid compound represented by the above-mentioned formula (IV) with an amine compound (V) while maintaining the stereostructure to prepare an epoxycarboxamide compound represented by the above-mentioned formula (I).

In this step, the epoxycarboxylic acid compound represented by the above-mentioned formula (IV) can be condensed with an amine compound represented by the above-mentioned formula (V) after converting the carboxyl group in epoxycarboxylic acid compound (IV) to a mixed acid anhydride using pivaloyl chloride, isobutyl chlorocarbonate, ethyl chlorocarbonate, p-toluene-sulfonyl chloride or methanesulfonyl chloride in the presence of a base such as triethylamine, pyridine and dimethyl-aminopyridine. It is desired that the reaction is effected in an inert solvent, and, for example, a halogenated hydrocarbon such as dichloromethane, chloroform and dichloroethane, an aromatic hydrocarbon such as benzene, toluene and xylene, an ether such as diethyl ether, dimethoxyethane, tetrahydrofuran and dioxane, dimethylformamide, acetonitrile, and ethyl acetate can be used individually or in combination. The reaction temperature can be −20° C. to 40° C.

The reaction between the epoxycarboxylic acid compound (IV) and the amine compound (V) can be carried out in the presence of a condensing agent, and, as the condensing agent, for example, a carbodiimide reagent such as dicyclohexylcarbodiimide, 1-ethyl-3-(3-dimethylaminopropyl)carbodiimide and iso-propylcarbodiimide can be used.

Further, in this step, the epoxycarboxylic acid compound (IV) is condensed with N-hydroxysuccinimide, p-nitrophenol or 1-hydroxybenzotriazole using the above-mentioned condensing agent to form an active ester product, and then the product formed can be reacted with the amine compound (V).

The epoxycarboxamide compound represented by the above-mentioned formula (I) is subjected to, for example, reaction in accordance with the formula mentioned below to stereoselectively form an azide compound represented by the above-mentioned formula (VI).

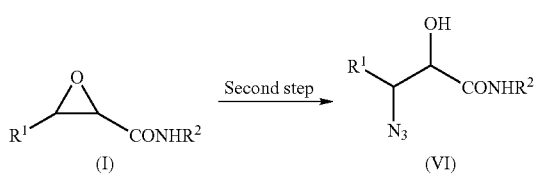

wherein R¹ and R² are, respectively, the same as R¹ and R² in the above-mentioned formula (I).

(Second Step)

This step is a step of subjecting the epoxycarboxamide compound represented by the above-mentioned formula (I) to regioselective ring-opening to stereoselectively prepare an azide compound represented by the above-mentioned formula (VI).

As a ring-opening agent to be used in this step, sodium azide-anhydrous magnesium sulfate can be used, and, instead of anhydrous magnesium sulfate, ammonium chloride can be used. As a reaction solvent, there may be used, for example, an alcohol solvent such as methanol, ethanol, propanol and 2-methoxyethanol, or acetonitrile. The reaction temperature can be 50° C. to 150° C.

In this step, the azide compounds (VI) shown in the following table can be stereoselectively prepared according to the respective stereostructures of the epoxycarboxamide compounds (I).

Incidentally, in the compound of the formula (VI), there are four optical isomers represented by the following formulae (VIa) to (VId), and all of these isomers are included in the present invention.

TABLE 2

| Epoxycarboxamide compound (I) | Azide compound (VIa) to (VId) |
| --- | --- |
| (Ia) | (VIa) |
| (Ib) | (VIb) |
| (Ic) | (VIc) |
| (Id) | (VId) |

In the table, R¹ and R² are, respectively, the same as R¹ and R² in the above-mentioned formula (I).

The azide compound represented by the above-mentioned formula (VI) is subjected to, for example, reaction in accor dance with the formula mentioned below to form an amine compound represented by the following formula (VII):

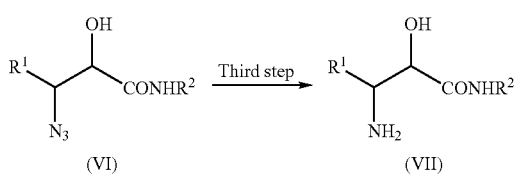

wherein $R^1$ and $R^2$ are, respectively, the same as $R^1$ and $R^2$ in the above-mentioned formula (I).

(Third Step)

This step is a step of reducing the azide compound represented by the above-mentioned formula (VI) while maintaining the stereostructure to prepare an amine compound represented by the above-mentioned formula (VII). The reaction in this step can be made using a general reduction reaction of an azide group to an amino group.

As a reduction reaction to be used in this step, a catalytic reduction method can be used, and, as a catalyst, there may be used, for example, Pd—C (palladium-carbon) or Pd black. As a reaction solvent, there may be used an alcohol solvent such as methanol and ethanol, and the reaction temperature can be room temperature to 40° C. The reaction pressure can be generally normal pressure to 200 atm., preferably normal pressure to 100 atm. Further, in this step, reduction can be carried out using triphenylphosphine and water, and it is preferred to use, as a reaction solvent, an ether solvent such as tetrahydrofuran and dioxane.

The amino alcohol compound represented by the above-mentioned formula (IX) can be prepared in accordance with the following reaction formula:

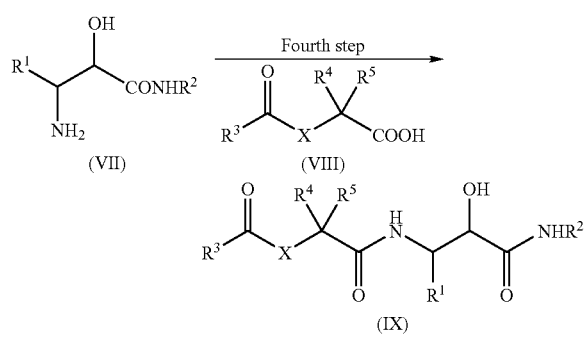

wherein $R^1$ to $R^5$ and X are, respectively, the same as $R^1$ to $R^5$ and X in the above-mentioned formula (IX).

(Fourth Step)

This step is a step of condensing the amine compound represented by the above-mentioned formula (VII) with a carboxylic acid compound represented by the above-mentioned formula (VIII) while maintaining the stereostructure to prepare an amino alcohol compound represented by the above-mentioned formula (IX).

The carboxylic acid compound represented by the above-mentioned formula (VIII) in this step can be condensed with an amine compound represented by the above-mentioned formula (VII) after converting the carboxyl group in carboxylic acid compound (VIII) to a mixed acid anhydride using pivaloyl chloride, isobutyl chlorocarbonate, ethyl chlorocarbonate, p-toluene-sulfonyl chloride or methanesulfonyl chloride in the presence of a base such as triethylamine, pyridine and dimethyl-aminopyridine. It is desired that the reaction is effected in an inert solvent, and, there may be used, for example, a halogenated hydrocarbon such as dichloromethane, chloroform and dichloroethane, an aromatic hydrocarbon such as benzene, toluene and xylene, an ether such as diethyl ether, dimethoxyethane, tetrahydrofuran and dioxane, dimethylformamide, acetonitrile and ethyl acetate individually or in combination. The reaction temperature can be $-20°$ C. to 40° C.

The reaction between the carboxylic acid compound (VIII) and the amine compound (VII) can be carried out in the presence of a condensing agent, and, as the condensing agent, there may be used, for example, a carbodiimide reagent such as dicyclohexylcarbodiimide, 1-ethyl-3-(3-dimethylaminopropyl)carbodiimide and isopropylcarbodiimide.

Moreover, in this step, the carboxylic acid compound (VIII) is condensed with N-hydroxysuccinimide, p-nitrophenol or 1-hydroxybenzotriazole using the above-mentioned condensing agent to form an active ester product, and then the product formed can be reacted with the amine compound (VII).

In this step, the amino alcohol compounds (IXa) to (IXd) shown in the following Table 3 having stereostructures maintained, respectively, corresponding to the stereostructures of the amine compounds (VIIa) to (VIId) can be prepared.

TABLE 3

| Amine compound (VIIa to VIId) | Amino alcohol compound (IXa to IXd) |
|---|---|
| 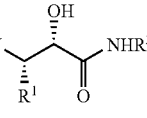 (VIIa) | 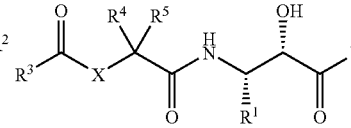 (IXa) |
| 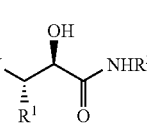 (VIIb) | 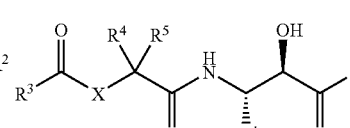 (IXb) |
| 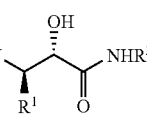 (VIIc) | 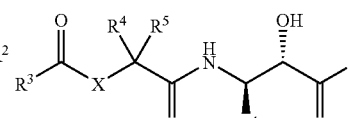 (IXc) |
| 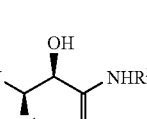 (VIId) | 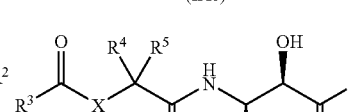 (IXd) |

In the table, $R^1$ to $R^5$ and X are, respectively, the same as $R^1$ to $R^5$ and X in the above-mentioned formula (IX).

The amino alcohol compound represented by the above-mentioned formula (IX) is subjected to, for example, reaction in accordance with the following formula to form an α-keto amide compound (X) having a cathepsin K inhibiting activity.

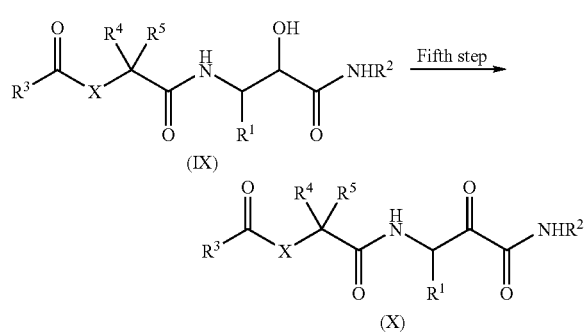

(IX)

(X)

wherein R¹ to R⁵ and X are, respectively, the same as R¹ to R⁵ and X in the above-mentioned formula (IX).

(Fifth Step)

This step is a step of oxidizing the amino alcohol compound represented by the above-mentioned formula (IX) to prepare an α-keto amide compound represented by the above-mentioned formula (X).

In this step, a general oxidation reaction of a hydroxy group to a ketone can be used. As an oxidation reaction to be used in this step, there may be used, for example, an active dimethyl sulfoxide oxidation method. As an oxidizing agent, dimethyl sulfoxide is used in combination with an activating agent such as dicyclohexylcarbodiimide, diphosphorus pentoxide, a pyridine-sulfur trioxide complex, oxalyl chloride, acetic anhydride and trifluoroacetic acid. The amount of the activating agent used is an equivalent amount to a 12 equivalent amount relative to the amino alcohol compound represented by the above-mentioned formula (IX). It is preferred that the reaction is effected in a solvent, and there may be used, for example, a halogenated hydrocarbon such as dichloromethane, chloroform and dichloroethane, or else, dimethyl sulfoxide as an oxidizing agent in an excess amount can be used as a solvent. The reaction can be advanced at −78° C. to 30° C.

In this step, the α-keto amide compounds (X) shown in the following Table 4 having stereostructures of R¹ maintained, respectively, corresponding to the stereostructures of the amino alcohol compounds (IX) can be prepared.

TABLE 4

| Amino alcohol compound (IXa to IXd) | α-Ketoamide compound (Xa to Xb) |
|---|---|
| (IXa) | (Xa) |
| (IXb) | |
| (IXc) | (Xb) |
| (IXd) | |

In the table, $R^1$ to $R^5$ and X are, respectively, the same as $R^1$ to $R^5$ and X in the above-mentioned formula (IX).

EXAMPLES

In the following, the present invention will be explained in more detail by referring to Reference Examples and Examples.

Reference Example 1

Synthesis of phenyl methyl 1-aminocyclohexanecarboxylate p-toluenesulfonate

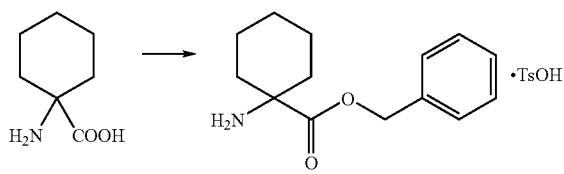

wherein TsOH represents p-toluenesulfonic acid.

In a flask were charged 50.8 g (355 mmol) of 1-aminocyclohexanecarboxylic acid, 81 g (426 mmol) of p-toluenesulfonic acid monohydrate, 180 ml of benzyl alcohol and 360 ml of toluene, and the mixture was heated overnight using a Dean-Stark device attached thereto a reflux condenser on an oil bath (160° C.). The formed water was removed by azeotropic distillation with toluene. After completion of the reaction, when the reaction mixture was poured into a large amount of ethyl acetate, crystals were precipitated. This crystal was washed again with ethyl acetate to obtain 128 g (Yield: 89%) of the title compound.

$^1$H-NMR (CDCl$_3$, δ): 1.25-1.43 (2H, m), 1.43-1.58 (2H, m), 1.59-1.70 (2H, m), 1.83-1.94 (2H, m), 1.94-2.02 (2H, m), 2.83 (3H, s), 5.13 (2H, s), 7.10 (2H, d, J=8 Hz), 7.24-7.31 (5H, m), 7.76 (2H, d, J=8 Hz), 8.30 (2H, brs)

IR (ν, KBr, cm$^{-1}$): 3468, 1746, 1608

FAB-Mass (m/z, %): 406 (M$^+$+1, 2), 234 (100)

Reference Example 2

Synthesis of phenylmethyl 1-[N-(morpholine-4-carbonyl)-amino]cyclohexanecarboxylate

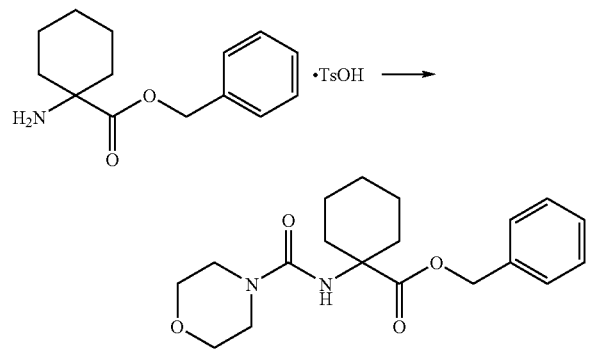

After neutralizing 203 g (500 mmol) of phenylmethyl 1-aminocyclohexanecarboxylate.p-toluenesulfonate with a 10% sodium carbonate solution, the mixture was extracted with chloroform and dried over anhydrous magnesium sulfate. The solid material was filtered off, and after adding 56 g (550 mmol) of triethylamine to the chloroform layer, 75 g (500 mmol) of 4-morpholinecarbonyl chloride was added dropwise, and the mixture was heated in an oil bath (60° C.) for 3 days. After completion of the reaction, the reaction mixture was washed successively in the order of water, a 10% aqueous potassium hydrogen sulfate solution, a saturated aqueous sodium hydrogen carbonate solution and a saturated NaCl solution, and dried over anhydrous sodium sulfate. After removing the solvent under reduced pressure, the resulting crystals were washed with ether to obtain 151 g (Yield: 87%) of the title compound.

$^1$H-NMR (CDCl$_3$, δ): 1.22-1.88 (6H, m), 1.85-1.92 (2H, m), 2.07-2.30 (2H, m), 3.45 (4H, t, J=5 Hz), 3.67 (4H, t, J=5 Hz), 4.53 (1H, s), 5.15 (2H, s), 7.31-7.34 (5H, m)

IR (ν, KBr, cm$^{-1}$): 3316, 1732, 1690

FAB-Mass (m/z, %): 347 (M$^+$+1, 100), 234 (44)

Reference Example 3

Synthesis of 1-[N-(morpholine-4-carbonyl)amino]cyclohexane-carboxylic acid

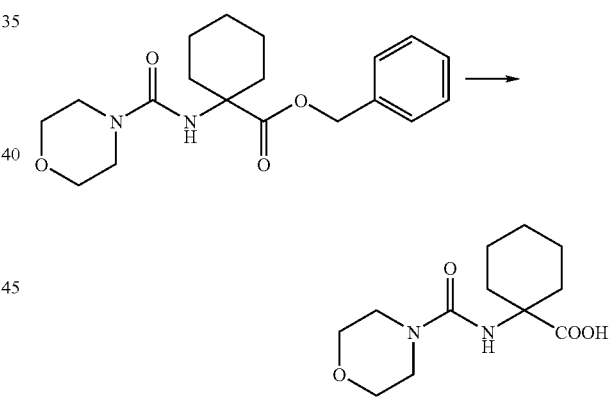

In methanol was suspended 151 g (452 mmol) of phenylmethyl 1-[N-(morpholine-4-carbonyl)amino]cyclohexanecarboxylate, 15 g of 5% palladium-active carbon was added to the suspension and the mixture was stirred under hydrogen stream at room temperature overnight. After removing the catalyst by filtration, the catalyst was washed three times with a mixed solvent of chloroform-methanol, and the organic layers were combined and the solvent was distilled off under reduced pressure to obtain 112 g (Yield: 100%) of the title compound.

$^1$H-NMR (CDCl$_3$, δ): 1.35-1.39 (3H, m), 1.64-1.72 (3H, m), 1.91-1.97 (2H, m), 2.06-2.10 (2H, m), 3.43 (4H, t, J=5 Hz), 3.73 (4H, t, J=5 Hz), 4.50 (1H, s)

IR (ν, KBr, cm$^{-1}$): 3824, 2568, 1970

FAB-Mass (m/z, %): 257 (M$^+$+1, 8), 98 (100)

Reference Example 4

Synthesis of 2-heptyne-1-ol

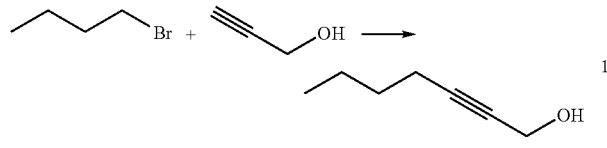

Lithium (6.0 g, 0.9 mol) was added to 300 ml of a liquid ammonia solution containing 180 mg (0.45 mmol) of iron (III) nitrate nonahydrate at −30 to −40° C. Moreover, at the same temperature, an ether solution (20 ml) containing 25.2 g (0.45 mol) of 2-propyne-1-ol was added to the mixture and after stirring for 1.5 hours, 41.1 g (0.30 mol) of n-butyl bromide was added to the mixture. The temperature of the reaction mixture was returned to room temperature and the mixture was stirred overnight. After completion of the reaction, a saturated aqueous ammonium chloride solution was added to the mixture and the resulting mixture was extracted with ether (500 ml). The organic layer was washed with a saturated NaCl solution, dried over anhydrous sodium sulfate, and then, the solvent was removed off under reduced pressure. The residue was distilled out under reduced pressure to obtain 21.0 g (Yield: 62.4%) of the title compound.

$^1$H-NMR (CDCl$_3$, δ): 0.91 (3H, t, J=7 Hz), 1.36-1.54 (5H, m), 2.22 (2H, tt, J=7 Hz, 2 Hz), 4.25 (1H, dt, J=6 Hz, 2 Hz)

Reference Example 5

Synthesis of (trans)-2-heptene-1-ol

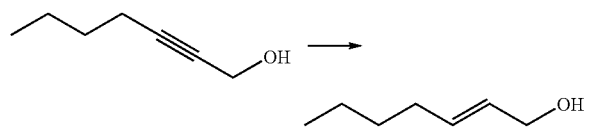

Under ice-cooling, to a toluene solution (5 ml) containing 4.0 g (35.66 mmol) of 2-heptyne-1-ol was added 16 ml (53.49 mmol) of a toluene solution containing 65% sodium bis(2-methoxy-ethoxy) aluminum hydride (Red-Al), and the temperature of the mixture was returned to room temperature and the mixture was stirred for 3 hours. After completion of the reaction, ice-water was added to the mixture and the resulting mixture was extracted with petroleum ether (50 ml). The organic layer was washed with a saturated NaCl solution, dried over anhydrous sodium sulfate, and the solvent was removed under reduced pressure. The residue was distilled out under reduced pressure to obtain 3.3 g (Yield: 80.6%) of the title compound.

$^1$H-NMR (CDCl$_3$, δ): 0.90 (3H, t, J=7 Hz), 1.27-1.41 (5H, m), 2.31 (2H, dt, J=7 Hz, 6 Hz), 4.09 (2H, dd, J=5 Hz, 5 Hz), 5.60-5.74 (2H, m)

Reference Example 6

Synthesis of (2R-trans)-3-butyloxiranemethanol

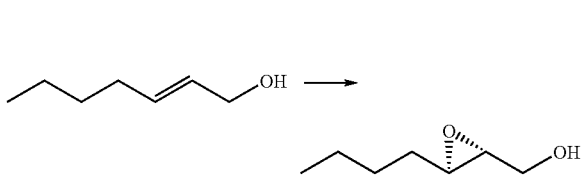

Under argon atmosphere, to anhydrous dichloromethane suspension (150 ml) containing 3.4 g of Molecular Sieves 4A were added 3.3 g (14.08 mmol) of diisopropyl D-(−)-tartarate, 3.3 g (11.73 mmol) of titanium tetraisopropoxide and 13.4 g (117.30 mmol) of (trans)-2-heptene-1-ol at −30 to −40° C. and the mixture was stirred for 10 minutes. The reaction mixture was cooled to −60° C., and under stirring, 105 ml of a toluene solution containing 2.23M of t-butylhydroperoxide was added dropwise to the mixture over 20 minutes, and the temperature of the resulting mixture was returned to room temperature over 2 hours. After completion of the reaction, the reaction mixture was added to an aqueous solution (400 ml) containing iron (III) sulfate heptahydrate (80 g) and L-tartaric acid (40 g), and the resulting mixture was extracted with dichloromethane (400 ml). The organic layer was washed with a saturated NaCl solution, dried over anhydrous sodium sulfate, and the solvent was removed under reduced pressure. To the residue were added ether (400 ml) and 1N-sodium hydroxide (200 ml), and the mixture was stirred at room temperature for one hour. After completion of the reaction, the organic layer was separated, and the aqueous layer was extracted with ether (50 ml). The organic layer was washed with a saturated NaCl solution, dried over anhydrous sodium sulfate, and the solvent was removed under reduced pressure. The residue was evaporated under reduced pressure to obtain 11.6 g (Yield: 76.2%) of the title compound.

$^1$H-NMR (CDCl$_3$, δ): 0.92 (3H, t, J=7 Hz), 1.34-1.48 (4H, m), 1.56-1.61 (2H, m), 1.73 (1H, brs), 2.91-2.98 (2H, m), 3.63 (1H, ddd, J=12 Hz, 8 Hz, 4 Hz), 3.92 (1H, ddd, J=12 Hz, 6 Hz, 3 Hz)

IR (ν, NaCl (film), cm$^{-1}$): 3456, 2936, 2864, 1470, 1030, 880

FAB-Mass (m/z, %): 131 (M$^+$+1, 58), 113 (84), 95 (100), 69 (93)

Reference Example 7

Synthesis of (2S-trans)-3-butyl-oxirane carboxylic acid.dicyclohexylammonium Salt

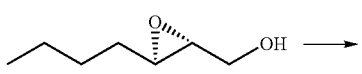

-continued

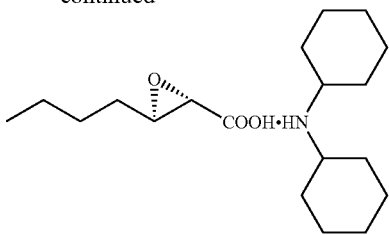

Under ice-cooling, to a mixed solution comprising 20 ml of acetonitrile, 20 ml of carbon tetrachloride and 30 ml of water containing 1.30 g (10 mmol) of (2R-trans)-3-butyloxirane methanol were added 5.70 g (25 mmol) of periodic acid, and then, 41 mg of ruthenium chloride n hydrate, and the resulting mixture was stirred at room temperature for one hour. Ethyl acetate was added to the reaction mixture, and after washing with water and then with a saturated NaCl solution, it was dried over anhydrous magnesium sulfate. Insoluble material was filtered off, and after adding 1.63 g (9 mmol) of dicyclohexyl amine to the filtrate, the solvent was removed under reduced pressure. Petroleum ether was added to the resulting residue and the mixture was stirred for 2 hours. The crystals were collected by filtration, and further washed with petroleum ether to obtain 2.30 g (Yield: 70%) of the title compound.

$^1$H-NMR (CDCl$_3$, δ): 0.91 (3H, t, J=7 Hz), 1.10-1.30 (6H, m), 1.31-1.57 (9H, m), 1.58-1.71 (3H, m), 1.74-1.82 (4H, m), 1.96-2.04 (4H, m), 2.90-2.94 (1H, m), 2.97-3.06 (2H, m), 3.08 (1H, d, J=2 Hz)

IR (ν, KBr, cm$^{-1}$): 2932, 2856, 1604, 1400

FAB-Mass (m/z, %): 326 (M$^+$+1, 7), 182 (100)

Example 1

Synthesis of (2S-trans)-N-[(1S,2S)-2-hydroxycyclohexane-1-yl]-3-butyloxiranecarboxamide (Compound of the formula I)

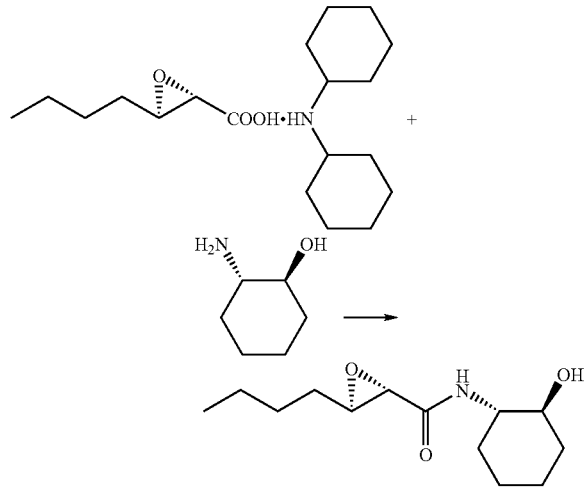

Under ice-cooling, to 20 ml of an anhydrous tetrahydrofuran solution containing 2.3 g (7 mmol) of (2S-trans)-3-butyloxirane carboxylic acid.dicyclohexylammonium salt was added 2 ml of an anhydrous tetrahydrofuran solution containing 844 mg (7 mmol) of pivaloyl chloride, and the mixture was stirred at the same temperature for 15 minutes. Moreover, the temperature of the reaction mixture was returned to room temperature and the mixture was further stirred for 2 hours. After removing insoluble material in the reaction mixture by filtration, the filtrate was added to 20 ml of an anhydrous tetrahydrofuran solution containing 806 mg (7 mmol) of (1S, 2S)-2-aminocyclohexanol under ice-cooling, and the resulting mixture was stirred at room temperature for 2 hours. Under reduced pressure, the reaction mixture was concentrated and ethyl acetate was added to the concentrate, and the resulting mixture was washed successively with a 10% aqueous potassium hydrogen sulfate solution, a saturated aqueous sodium hydrogen carbonate solution, and then, a saturated NaCl solution. The organic layer was dried over anhydrous magnesium sulfate, and the solvent was removed under reduced pressure to obtain 1.69 g (Yield: 100%) of the title compound.

$^1$H-NMR (CDCl$_3$, δ): 0.92 (3H, t, J=7 Hz), 1.11-1.48 (8H, m), 1.52-1.62 (1H, m), 1.64-1.76 (3H, m), 1.83-1.89 (1H, m), 2.03-2.10 (1H, m), 2.90-2.95 (1H, m), 3.27 (1H, d, J=2 Hz), 3.30-3.38 (1H, m), 3.54-3.65 (1H, m), 6.13 (1H, d, J=8 Hz)

IR (ν, KBr, cm$^{-1}$): 2932, 2860, 1650

FAB-Mass (m/z, %): 242 (M$^+$+1, 100), 98 (95)

Example 2

Synthesis of (2S,3S)-N-[(1S,2S)-2-hydroxycyclohexane-1-yl]-3-azido-2-hydroxyheptanamide (Compound of the formula VI)

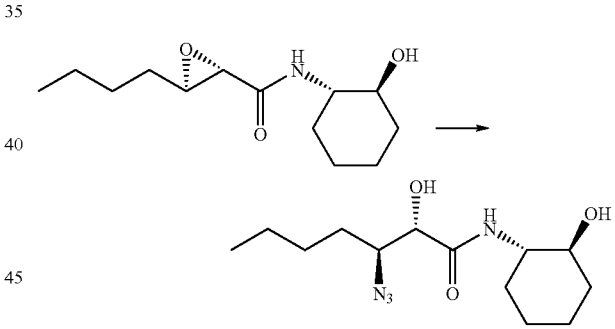

30 ml of a methanol suspension containing 1.64 g (7 mmol) of (2S)-trans-N-[(1S,2S)-2-hydroxycyclohexane-1-yl]-3-butyloxiranecarboxamide, 910 mg (14 mmol) of sodium azide and 868 mg (7.2 mmol) of anhydrous magnesium sulfate was refluxed for 5 hours. After the temperature of the reaction mixture was returned to room temperature, the reaction mixture was poured into 300 ml of water and the resulting mixture was stirred for 2 hours. The resulting crystals were collected by filtration and washed with water, and dried to obtain 1.45 g (Yield: 73%) of the title compound.

$^1$H-NMR (CDCl$_3$, δ): 0.91 (3H, t, J=7 Hz), 1.19-1.53 (9H, m), 1.58-1.78 (3H, m), 1.89-1.98 (1H, m), 2.03-2.11 (1H, m), 3.31-3.39 (1H, m), 3.52 (1H, d, J=6 Hz), 3.61-3.71 (2H, m), 4.15 (1H, d, J=4 Hz), 4.29 (1H, t, J=4 Hz), 6.78 (1H, d, J=8 Hz)

IR (ν, KBr, cm$^{-1}$): 2936, 2864, 2096, 1636

FAB-Mass (m/z, %): 285 (M$^+$+1, 100), 116 (97)

Reference Example 8

Synthesis of (2S,3S)-N-[(1S,2S)-2-hydroxycyclohexane-1-yl]-3-amino-2-hydroxyheptanamide (Compound of the formula VII)

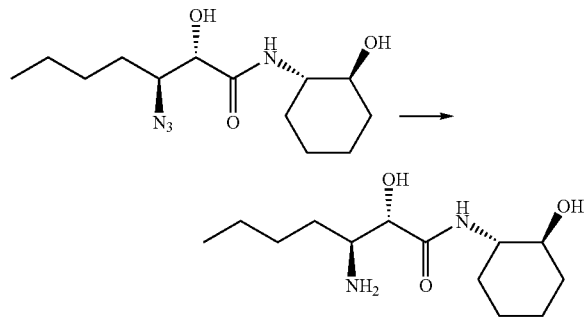

To 30 ml of a methanol solution containing 1.45 g (5 mmol) of (2S,3S)-N-[(1S,2S)-2-hydroxycyclohexane-1-yl]-3-azido-2-hydroxyheptanamide was added 150 mg of 5% palladium carbon, and the resulting mixture was stirred under hydrogen atmosphere for 18 hours. Insoluble material was filtered off, and the filtrate was distilled under reduced pressure to obtain 1.18 g (Yield: 91%) of the title compound.

$^1$H-NMR (CDCl$_3$, δ): 0.90 (3H, t, J=7 Hz), 1.18-1.43 (8H, m), 1.51-1.77 (4H, m), 1.89-1.97 (1H, m), 2.02-2.09 (1H, m), 3.03-3.09 (1H, m), 3.31-3.39 (1H, m), 3.61-3.69 (1H, m), 3.90 (1H, d, J=6 Hz), 7.31 (1H, d, J=8 Hz)

IR (ν, KBr, cm$^{-1}$): 3344, 2936, 2860, 1650

FAB-Mass (m/z, %): 259 (M$^+$+1, 100), 86 (92)

Example 3

Synthesis of N-[(2S,3S)-2-hydroxy-1-[N-[(1S,2S)-2-hydroxy-cyclohexane-1-yl]amino]-1-oxo-3-heptyl]-1-[N-(morpholine-4-carbonyl)amino]cyclohexane carboxamide (Compound of the Formula IX)

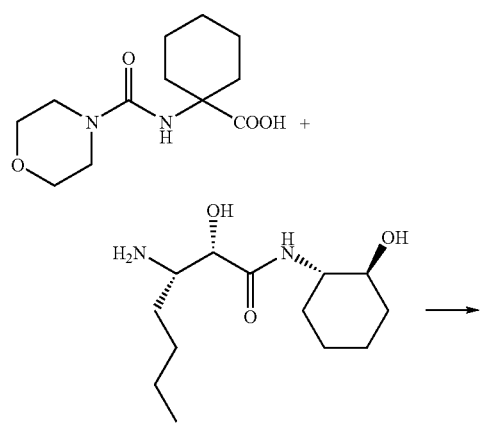

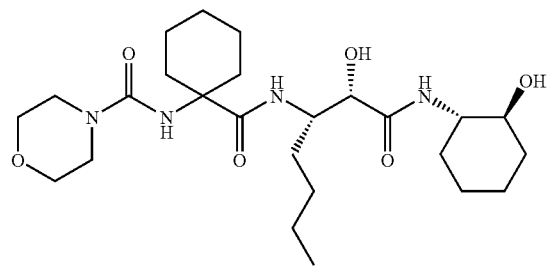

Under ice-cooling, to 10 ml of an anhydrous tetrahydrofuran solution containing 256 mg (1 mmol) of 1-[N-(morpholine-4-carbonyl)amino]cyclohexanecarboxylic acid and 202 mg (2 mmol) of triethylamine was added 1 ml of an anhydrous tetrahydrofuran solution containing 121 mg (1 mmol) of pivaloyl chloride, and the resulting mixture was stirred at the same temperature for 2 hours. Moreover, the temperature of the reaction mixture was returned to room temperature and the mixture was stirred for 18 hours. Insoluble material in the reaction mixture was filtered off, and the filtrate was added to 80 ml of a chloroform solution containing 258 mg (1 mmol) of (2S,3S)-N-[(1S,2S)-2-hydroxycyclohexane-1-yl]-3-amino-2-hydroxyheptanamide, and the resulting mixture was stirred for 3 hours. Chloroform was additionally added to the reaction mixture, and the resulting mixture was washed successively with a 10% aqueous potassium hydrogen sulfate solution, a saturated aqueous sodium hydrogen carbonate solution and then a saturated NaCl solution, dried over anhydrous magnesium sulfate and the solvent was removed under reduced pressure. The residue was purified by silica gel column chromatography to obtain 468 mg (Yield: 94%) of the title compound.

$^1$H-NMR (CDCl$_3$, δ): 0.88 (3H, t, J=7 Hz), 1.17-1.44 (11H, m), 1.45-1.58 (1H, m), 1.59-1.77 (6H, m), 1.82-1.97 (4H, m), 2.01-2.07 (2H, m), 3.31-3.44 (5H, m), 3.59-3.69 (1H, m), 3.72 (4H, t, J=5 Hz), 3.76 (1H, d, J=4 Hz), 4.05-4.14 (2H, m), 4.75 (1H, s), 5.02 (1H, d, J=6 Hz), 6.56 (1H, d, J=8 Hz), 7.03 (1H, d, J=8 Hz)

IR (ν, KBr, cm$^{-1}$): 3380, 2931, 2859, 1675, 1629

FAB-Mass (m/z, %): 497 (M$^+$+1, 55), 211 (100)

Reference Example 9

Synthesis of N-[(S)-1,2-dioxo-1-[N-[(S)-2-oxocyclohexyl]-amino]-3-heptyl]-1-[N-(morpholine-4-carbonyl)amino]cyclohexanecarboxamide (Compound of the formula X)

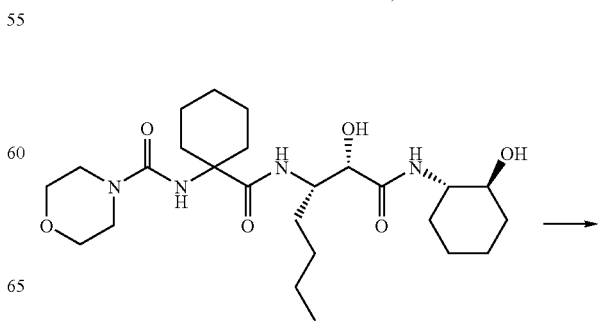

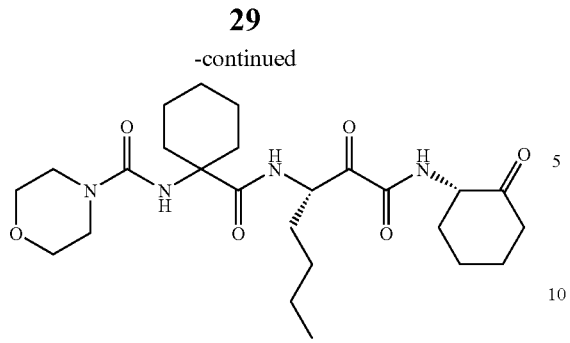

Under nitrogen stream, at 0° C., 1.45 g (11.2 mmol) of N,N-diisopropylethylamine was added dropwise to a mixed solution of anhydrous dimethylsulfoxide (5 ml) and anhydrous dichloromethane (5 ml) containing 1.78 g (11.2 mmol) of sulfur trioxide pyridine complex salt. Moreover, to the mixture was added an anhydrous dichloromethane (5 ml) solution containing 465 mg (0.94 mmol) of N-[(2S,3S)-2-hydroxy-1-[N-[(1S,2S)-2-hydroxycyclohexane-1-yl]amino]-1-oxo-3-heptyl]-1-[N-(morpholine-4-carbonyl)amino]cyclohexanecarboxamide, and the resulting mixture was stirred at 0° C. for 3 hours. After completion of the reaction, ice-water was added to the reaction mixture, and the resulting mixture was extracted with ethyl acetate. The organic layer was washed successively with a 10% aqueous citric acid solution, a saturated aqueous sodium hydrogen carbonate solution and a saturated NaCl solution, dried over anhydrous magnesium sulfate, and concentrated under reduced pressure. The residue was purified by neutral silica gel column chromatography to obtain 402 mg (Yield: 87%) of the title compound.

$^1$H-NMR (CDCl$_3$, δ): 0.88 (3H, t, J=7 Hz), 1.23-1.46 (8H, m), 1.56-2.00 (10H, m), 2.03-2.20 (3H, m), 2.36-2.70 (3H, m), 3.39 (4H, t, J=5 Hz), 3.72 (4H, t, J=5 Hz), 4.36-4.47 (1H, m), 4.46 (1H, s), 5.20-5.25 (1H, m), 7.76 (1H, d, J=6 Hz), 7.93 (1H, d, J=7 Hz)

IR (ν, KBr, cm$^{-1}$): 3380, 2931, 2859, 1675, 1629

FAB-Mass (m/z, %): 493 (M$^+$+1, 25), 239 (54), 211 (100)

Example 4

Synthesis of (2S-trans)-N-[(3,4-methylenedioxy)phenyl]-3-butyloxiranecarboxamide (Compound of the formula I)

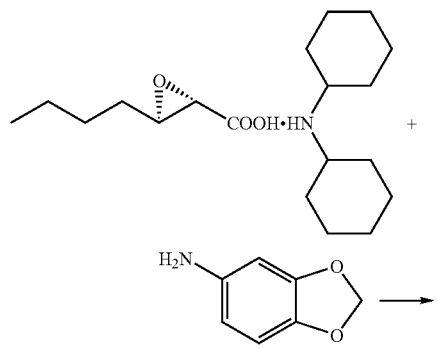

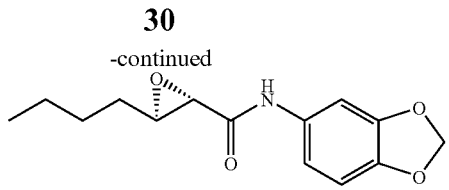

Under ice-cooling, to 10 ml of an anhydrous tetrahydrofuran solution containing 299 mg (1.84 mmol) of (2S-trans)-3-butyl-oxiranecarboxylic acid.dicyclohexylammonium salt was added 2 ml of an anhydroustetrahydrofuran solution containing 222 mg (1.84 mmol) of pivaloyl chloride, and the resulting mixture was stirred at the same temperature for 15 minutes. Moreover, the temperature of the reaction mixture was returned to room temperature, and the mixture was stirred for 2 hours. After insoluble material in the reaction mixture was filtered off, the filtrate was added to 10 ml of an anhydrous tetrahydrofuran solution containing 252 mg (1.84 mmol) of 3,4-methylene-dioxyaniline under ice-cooling, and the resulting mixture was stirred at room temperature for 2 hours. Under reduced pressure, the reaction mixture was concentrated, ethyl acetate was added to the concentrate, and the resulting mixture was washed successively with a 10% aqueous potassium hydrogen sulfate solution, a saturated aqueous sodium hydrogen carbonate solution and then a saturated NaCl solution. The organic layer was dried over anhydrous magnesium sulfate, and the solvent was removed under reduced pressure to obtain 484 mg (Yield: 100%) of the title compound.

$^1$H-NMR (CDCl$_3$, δ): 0.93 (3H, t, J=7 Hz), 1.22-1.51 (4H, m), 1.58-1.80 (2H, m), 3.05-3.09 (1H, m), 3.33 (1H, d, J=2 Hz), 5.95 (2H, s), 6.74 (1H, d, J=8 Hz), 6.81 (1H, dd, J=8 Hz, 2 Hz), 7.25 (1H, d, J=2 Hz), 7.72 (1H, s)

IR (ν, NaCl, cm$^{-1}$): 2932, 2872, 1674

Example 5

Synthesis of (2S,3S)-N-[(3,4-methylenedioxy)phenyl]-3-azido-2-hydroxyheptanamide (Compound of the formula VI)

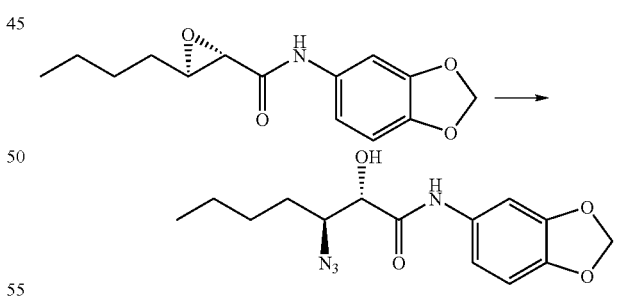

30 ml of a methanol suspension containing 484 mg (1.84 mmol) of (2S-trans)-N-[(3,4-methylenedioxy)phenyl]-3-butyl-oxiranecarboxamide, 239 mg (3.68 mmol) of sodium azide and 228 mg (1.89 mmol) of anhydrous magnesium sulfate was refluxed for 5 hours. After the temperature of the reaction mixture was returned to room temperature, the reaction mixture was concentrated under reduced pressure, ethyl acetate was added to the concentrate, and the resulting mixture was washed successively with water, and then, with a saturated NaCl solution. The organic layer was dried over anhydrous magnesium sulfate, and the solvent was removed under reduced pressure. The residue was purified by silica gel column chromatography to obtain 395 mg (Yield: 70%) of the title compound.

$^1$H-NMR (CDCl$_3$, δ): 0.91 (3H, t, J=7 Hz), 1.30-1.41 (2H, m), 1.42-1.80 (4H, m), 3.04 (1H, brs), 3.82-3.85 (1H, m), 4.40 (1H, d, J=4 Hz), 5.96 (2H, s), 6.76 (1H, d, J=8 Hz), 6.86 (1H, dd, J=8 Hz, 2 Hz), 7.27 (1H, d, J=2 Hz), 8.32 (1H, s)

IR (v, NaCl, cm$^{-1}$): 2932, 2872, 2104, 1658

Reference Example 10

Synthesis of (2S,3S)-N-[(3,4-methylenedioxy)phenyl]-3-amino-2-hydroxyheptanamide (Compound of the formula VII)

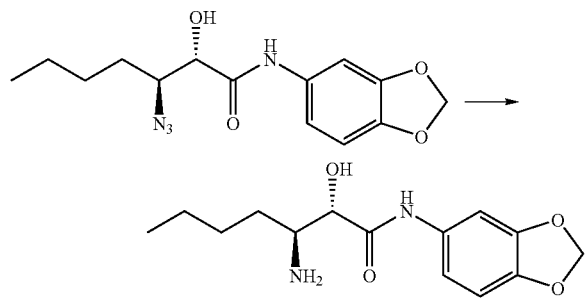

To 30 ml of a methanol solution containing 395 mg (1.29 mmol) of (2S,3S)-N-[(3,4-methylenedioxy)phenyl]-3-azido-2-hydroxyheptanamide was added 40 mg of 5% palladium carbon, and the resulting mixture was stirred under hydrogen atmosphere for 18 hours. Insoluble materials were filtered off, and the filtrate was distilled under reduced pressure to obtain 344 mg (Yield: 95%) of the title compound.

$^1$H-NMR (CDCl$_3$, δ): 0.91 (3H, t, J=7 Hz), 1.20-1.75 (6H, m), 3.10 (1H, brs), 3.92 (1H, d, J=6 Hz), 5.95 (1H, d, J=6 Hz), 5.95 (2H, s), 6.76 (1H, d, J=8 Hz), 6.86 (1H, dd, J=8 Hz, 2 Hz), 7.28 (1H, d, J=2 Hz), 9.81 (1H, s)

IR (v, KBr, cm$^{-1}$): 3384, 2956, 2872, 1658

Example 6

Synthesis of N-[(2S,3S)-2-hydroxy-1-[N-[(3,4-methylene-dioxy)phenyl]amino]-1-oxo-3-heptyl]-1-[N-(morpholine-4-carbonyl)amino]cyclohexanecarboxamide (Compound of the formula IX)

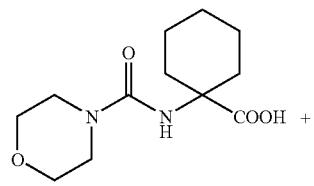

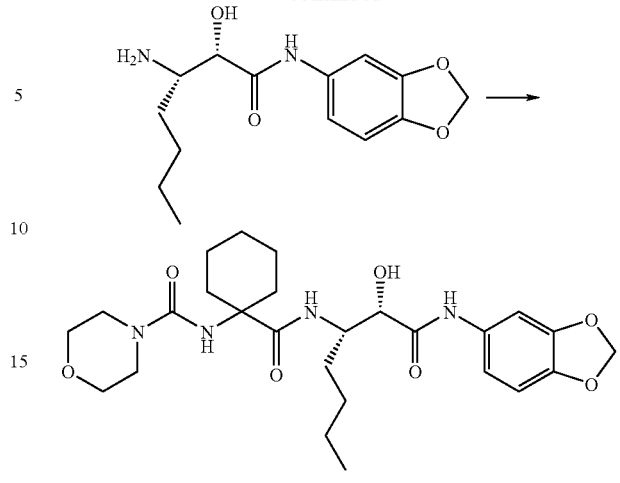

In anhydrous dichloromethane were dissolved 344 mg (1.23 mmol) of (2S,3S)-N-[(3,4-methylenedioxy)phenyl]-3-amino-2-hydroxyheptanamide, 315 mg (1.23 mmol) of 1-[N-(morpholine-4-carbonyl)amino]cyclohexanecarboxylic acid and 233 mg (1.48 mmol) of 1-hydroxybenzotriazole, and then, under nitrogen stream, 284 mg (1.48 mmol) of 1-ethyl-3-(3-dimethyl-aminopropyl)carbodiimide was added to the above mixture at 0° C. Thereafter, the temperature of the reaction mixture was returned to room temperature, and the mixture was stirred overnight. The reaction mixture was concentrated under reduced pressure, the residue was dissolved in 80 ml of ethyl acetate, and the resulting mixture was washed successively with water, a 10% aqueous potassium hydrogen sulfate solution, a saturated aqueous sodium hydrogen carbonate solution and a saturated NaCl solution, dried over anhydrous magnesium sulfate and concentrated under reduced pressure. The residue was purified by silica gel column chromatography to obtain 574 mg (Yield: 90%) of the desired compound.

$^1$H-NMR (CDCl$_3$, δ): 0.88 (3H, t, J=7 Hz), 1.24-1.42 (6H, m), 1.52-1.72 (10H, m), 1.80-2.10 (4H, m), 3.32 (4H, t, J=5 Hz), 3.67 (4H, t, J=5 Hz), 4.19-4.22 (1H, m), 4.41-4.43 (1H, m), 4.64 (1H, s), 5.50 (1H, d, J=6 Hz), 5.94 (2H, s), 6.70 (1H, d, J=8 Hz), 6.89 (1H, dd, J=8 Hz, 2 Hz), 7.33 (1H, d, J=2 Hz), 8.69 (1H, s)

IR (v, KBr, cm$^{-1}$): 3384, 2932, 2860, 1658

Reference Example 11

Synthesis of N-[(S)-1,2-dioxo-1-[N-[(3,4-methylenedioxy)-phenyl]amino]-3-heptyl]-1-[N-(morpholine-4-carbonyl)amino]-cyclohexanecarboxamide (Compound of the formula X)

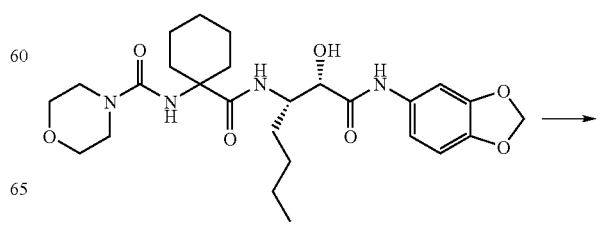

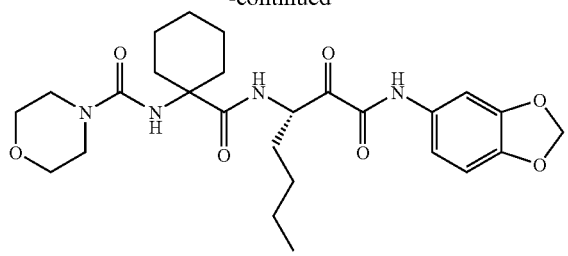

Under nitrogen stream and at 0° C., 861 mg (6.66 mmol) of N,N-diisopropylethylamine was added dropwise to a mixed solution of anhydrous dimethylsulfoxide (5 ml) and anhydrous dichloro-methane (5 ml) containing 1.06 g (6.66 mmol) of sulfur trioxide pyridine complex salt. Moreover, an anhydrous dichloromethane (5 ml) solution containing 574 mg (1.11 mmol) of N-[(2S,3S)-2-hydroxy-1-[N-(3,4-methylenedioxyphenyl-1-yl)amino]-1-oxo-3-heptyl]-1-[N-(morpholine-4-carbonyl)amino]cyclohexane-carboxamide was added to the above mixture, and the resulting mixture was stirred at 0° C. for 3 hours. After completion of the reaction, ice-water was added to the reaction mixture, and the resulting mixture was extracted with ethyl acetate. The organic layer was washed successively with a 10% aqueous citric acid solution, a saturated aqueous sodium hydrogen carbonate solution and a saturated NaCl solution, dried over anhydrous magnesium sulfate, and then, concentrated under reduced pressure. The residue was purified by neutral silica gel column chromatography to obtain 499 mg (Yield: 87%) of the title compound.

$^1$H-NMR (CDCl$_3$, δ): 0.89 (3H, t, J=7 Hz), 1.28-1.42 (7H, m), 1.58-1.72 (4H, m), 1.85-2.17 (5H, m), 3.37 (4H, t, J=5 Hz), 3.71 (4H, t, J=5 Hz), 4.43 (1H, s), 5.20-5.26 (1H, m), 5.97 (2H, s), 6.77 (1H, d, J=8 Hz), 6.95 (1H, dd, J=8 Hz, 2 Hz), 7.35 (1H, d, J=2 Hz), 8.06 (1H, d, J=7 Hz), 8.56 (1H, s)

IR (ν, KBr, cm$^{-1}$): 2928, 2860, 1666

Example 7

Synthesis of (2S-trans)-N-butyl-3-butyloxiranecarboxamide (Compound of the formula I)

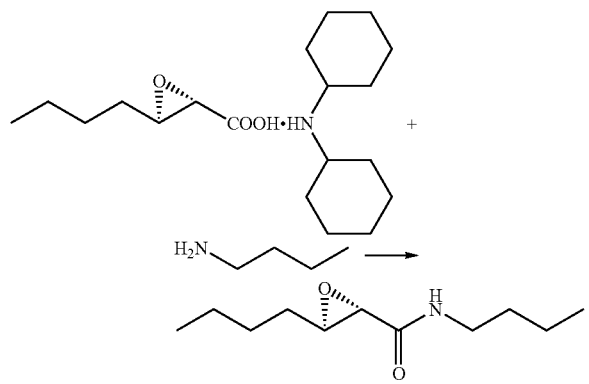

Under ice-cooling, to 10 ml of an anhydrous tetrahydrofuran solution containing 299 mg (1.84 mmol) of (2S-trans)-3-butyl-oxiranecarboxylic acid-dicyclohexylammonium salt was added 2 ml of an anhydrous tetrahydrofuran solution containing 222 mg (1.84 mmol) of pivaloyl chloride, and the resulting mixture was stirred at the same temperature for 15 minutes. Moreover, the temperature of the reaction mixture was returned to room temperature, and the mixture was stirred for 2 hours. After filtering off insoluble materials in the reaction mixture, the filtrate was added to 10 ml of an anhydrous tetrahydrofuran solution containing 135 mg (1.84 mmol) of n-butylamine under ice-cooling, and the resulting mixture was stirred at room temperature for 2 hours. Under reduced pressure, the reaction mixture was concentrated and ethyl acetate was added to the concentrate, and the resulting mixture was washed successively with a 10% aqueous potassium hydrogen sulfate solution, a saturated aqueous sodium hydrogen carbonate solution and then a saturated NaCl solution. The organic layer was dried over anhydrous magnesium sulfate, and the solvent was removed under reduced pressure to obtain 366 mg (Yield: 100%) of the title compound.

$^1$H-NMR (CDCl$_3$, δ): 0.93 (3H, t, J=7 Hz), 0.94 (3H, t, J=7 Hz), 1.26-1.70 (10H, m), 2.89-2.93 (1H, m), 3.17-3.25 (3H, m), 6.10 (1H, s)

IR (ν, NaCl, cm$^{-1}$): 2932, 2872, 1662

Example 8

Synthesis of (2S,3S)-N-butyl-3-azido-2-hydroxyheptanamide (Compound of the formula VI)

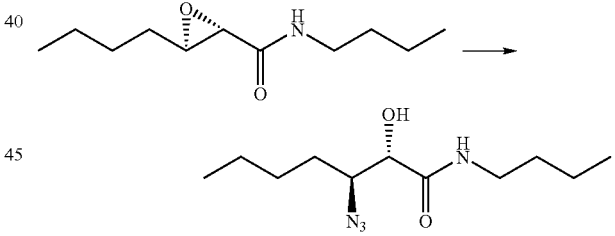

A suspension of 30 ml of methanol containing 366 mg (1.84 mmol) of (2S-trans)-N-butyl-3-butyloxiranecarboxamide, 239 mg (3.68 mmol) of sodium azide and 228 mg (1.89 mmol) of anhydrous magnesium sulfate was refluxed for 5 hours. After the temperature of the reaction mixture was returned to room temperature, the reaction mixture was concentrated under reduced pressure, ethyl acetate was added to the concentrate, and the resulting mixture was washed successively with water, and then a saturated NaCl solution. The organic layer was dried over anhydrous magnesium sulfate, and the solvent was removed under reduced pressure. The residue was purified by silica gel column chromatography to obtain 304 mg (Yield: 68%) of the title compound.

$^1$H-NMR (CDCl$_3$, δ): 0.93 (3H, t, J=7 Hz), 0.95 (3H, t, J=7 Hz), 1.20-1.70 (10H, m), 2.86 (1H, d, J=4 Hz), 3.25-3.35 (2H, m), 3.68-3.72 (1H, m), 4.21 (1H, t, J=4 Hz), 6.54 (1H, brs)

IR (ν, NaCl, cm$^{-1}$): 2960, 2872, 2100, 1648

Reference Example 12

Synthesis of (2S,3S)-N-butyl-3-amino-2-hydroxyheptanamide (Compound of the formula VII)

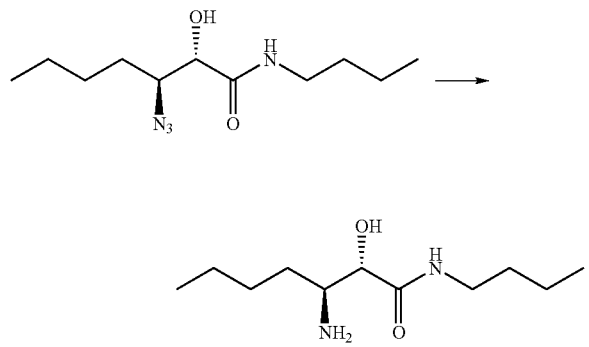

To 30 ml of a methanol solution containing 304 mg (1.25 mmol) of (2S,3S)-N-butyl-3-azido-2-hydroxyheptanamide was added 30 mg of 5% palladium carbon, and the resulting mixture was stirred under hydrogen atmosphere for 18 hours. Insoluble materials were filtered off, and the filtrate was distilled under reduced pressure to obtain 254 mg (Yield: 94%) of the title compound.

$^1$H-NMR (CDCl$_3$, δ): 0.91 (3H, t, J=7 Hz), 0.93 (3H, t, J=7 Hz), 1.18-1.80 (10H, m), 3.01-3.50 (1H, m), 3.23-3.29 (3H, m), 3.83 (1H, d, J=5 Hz), 7.45 (1H, brs)

IR (ν, KBr, cm$^{-1}$): 3320, 2932, 2860, 1642

Example 9

Synthesis of N-[(2S,3S)-2-hydroxy-1-[N-(butyl)amino]-1-oxo-3-heptyl]-1-[N-(morpholine-4-carbonyl)amino]cyclohexane-carboxamide (Compound of the formula IX)

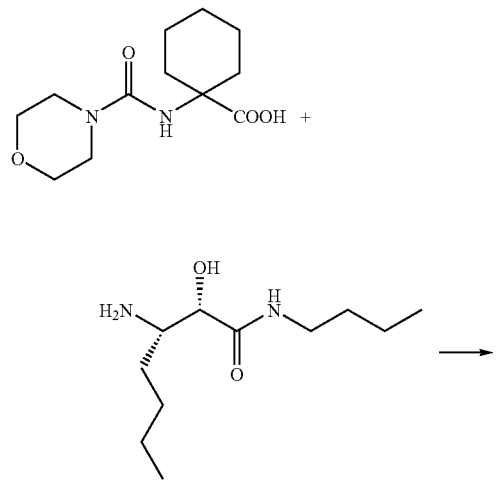

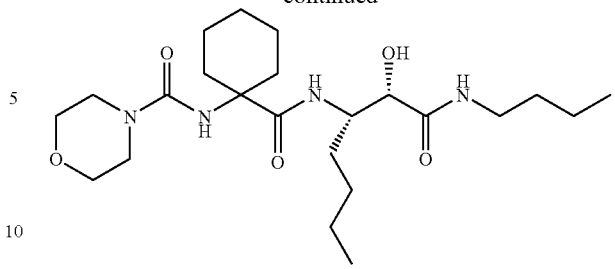

In anhydrous dichloromethane were dissolved 254 mg (1.21 mmol) of (2S,3S)-N-butyl-3-amino-2-hydroxyheptanamide, 310 mg (1.21 mmol) of 1-[N-(morpholine-4-carbonyl)amino]cyclohexanecarboxylic acid and 230 mg (1.45 mmol) of 1-hydroxy-benzotriazole, subsequently, under nitrogen stream, 278 mg (1.45 mmol) of 1-ethyl-3-(3-dimethylaminopropyl)carbodiimide was added to the solution at 0° C. Thereafter, the temperature of the reaction mixture was returned to room temperature and the mixture was stirred overnight. The reaction mixture was concentrated under reduced pressure, the residue was dissolved in 80 ml of ethyl acetate, and the resulting mixture was washed successively with water, a 10% aqueous potassium hydrogen sulfate solution, a saturated aqueous sodium hydrogen carbonate solution and a saturated NaCl solution, dried over anhydrous magnesium sulfate, and concentrated under reduced pressure. The residue was purified by silica gel column chromatography to obtain 489 mg (Yield: 89%) of the desired compound.

$^1$H-NMR (CDCl$_3$, δ): 0.87 (3H, t, J=7 Hz), 0.94 (3H, t, J=7 Hz), 1.24-1.41 (8H, m), 1.45-1.78 (8H, m), 1.84-1.94 (2H, m), 1.98-2.05 (2H, m), 3.18-3.30 (2H, m), 3.70 (4H, t, J=5 Hz), 3.89 (4H, t, J=5 Hz), 4.10-4.14 (1H, m), 4.26 (1H, dd, J=6 Hz, 6 Hz), 4.65 (1H, s), 5.18 (1H, d, J=6 Hz), 6.73 (1H, d, J=8 Hz), 6.80 (1H, brs)

IR (ν, KBr, cm$^{-1}$): 3368, 2932, 2860, 1650

Reference Example 13

Synthesis of N-[(S)-1,2-dioxo-1-[N-(butyl)amino]-3-heptyl]-1-[N-[(morpholine-4-carbonyl)amino]cyclohexanecarboxamide (Compound of the formula X)

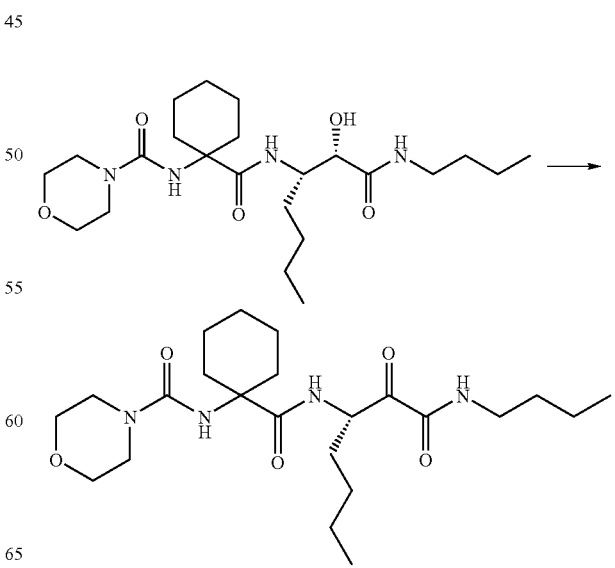

Under nitrogen stream, 838 mg (6.48 mmol) of N,N-diisopropylethylamine was added dropwise at 0° C. to a mixed solution of anhydrous dimethylsulfoxide (5 ml) and anhydrous dichloro-methane (5 ml) containing 1.03 g (6.48 mmol) of sulfur trioxide pyridine complex salt. Moreover, to the above mixture was added an anhydrous dichloromethane (5 ml) solution containing 489 mg (1.08 mmol) of N-[(2S,3S)-2-hydroxy-1-[N-(butyl)-amino]-1-oxo-3-heptyl]-1-[N-(morpholine-4-carbonyl)amino]cyclohexanecarboxamide, and the resulting mixture was stirred at 0° C. for 3 hours. After completion of the reaction, ice-water was added to the reaction mixture, and the resulting mixture was extracted with ethyl acetate. The organic layer was washed successively with a 10% aqueous citric acid solution, a saturated aqueous sodium hydrogen carbonate solution and a saturated NaCl solution, dried over anhydrous magnesium sulfate, and concentrated under reduced pressure. The residue was purified by neutral silica gel column chromatography to obtain 415 mg (Yield: 85%) of the title compound.

$^1$H-NMR (CDCl$_3$, δ): 0.88 (3H, t, J=7 Hz), 0.93 (3H, t, J=7 Hz), 1.22-1.42 (9H, m), 1.49-1.70 (6H, m), 1.85-2.00 (3H, m), 2.06-2.15 (2H, m), 3.26-3.38 (2H, m), 3.38 (4H, t, J=5 Hz), 3.72 (4H, t, J=5 Hz), 4.44 (1H, s), 5.17-5.20 (1H, m), 6.86 (1H, t, J=6 Hz), 7.94 (1H, d, J=7 Hz)

IR (ν, KBr, cm$^{-1}$): 3344, 2932, 2860, 1658

Example 10

Synthesis of (2S-trans)-N-[(2S)-1-methoxy-1-oxo-3-phenyl-2-propyl]-3-butyloxiranecarboxamide (Compound of the formula I)

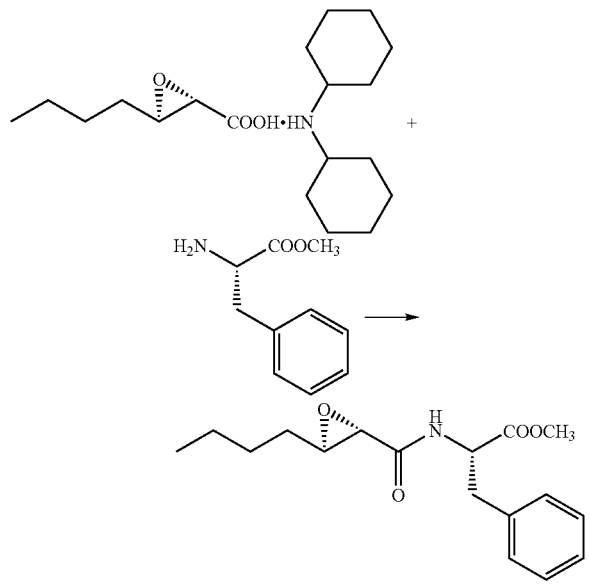

Under ice-cooling, to 10 ml of an anhydrous tetrahydrofuran solution containing 299 mg (1.84 mmol) of (2S-trans)-3-butyl-oxirane carboxylic acid.dicyclohexylammonium salt was added 2 ml of an anhydrous tetrahydrofuran solution containing 222 mg (1.84 mmol) of pivaloyl chloride, and the resulting mixture was stirred at the same temperature for 15 minutes. Moreover, the temperature of the reaction mixture was returned to room temperature and the mixture was stirred for 2 hours. After filtering off insoluble materials in the reaction mixture, 187 mg (1.84 mmol) of triethylamine was added to the filtrate under ice-cooling, and then, 397 mg (1.84 mmol) of L-phenylalanine methyl ester hydrochloride was added to the mixture, and the resulting mixture was stirred at room temperature for 2 hours. Under reduced pressure, the reaction mixture was concentrated and ethyl acetate was added to the concentrate, and the resulting mixture was washed successively with a 10% aqueous potassium hydrogen sulfate solution, a saturated aqueous sodium hydrogen carbonate solution and then a saturated NaCl solution. The organic layer was dried over anhydrous magnesium sulfate, and the solvent was removed under reduced pressure to obtain 558 mg (Yield: 100%) of the title compound.

$^1$H-NMR (CDCl$_3$, δ): 0.91 (3H, t, J=7 Hz), 1.20-1.45 (4H, m), 1.46-1.63 (2H, m), 2.58-2.61 (1H, m), 3.01 (1H, dd, J=14 Hz, 7 Hz), 3.16 (1H, d, J=2 Hz), 3.20 (1H, dd, J=14 Hz, 7 Hz), 3.74 (3H, s), 4.81-4.87 (1H, m), 6.48 (1H, d, J=8 Hz), 7.05-7.10 (2H, m), 7.24-7.31 (3H, m)

IR (ν, NaCl, cm$^{-1}$): 2960, 2868, 1684

Example 11

Synthesis of (2S,3S)-N-[(2S)-1-methoxy-1-oxo-3-phenyl-2-propyl]-3-azido-2-hydroxyheptanamide (Compound of the formula VI)

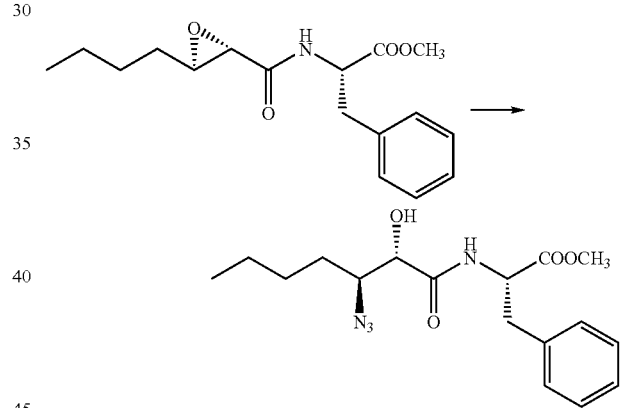

A suspension of 30 ml of methanol containing 558 mg (1.84 mmol) of (2S-trans)-N-[(2S)-1-methoxy-1-oxo-3-phenyl-2-propyl]-3-butyloxiranecarboxamide, 239 mg (3.68 mmol) of sodium azide and 228 mg (1.89 mmol) of anhydrous magnesium sulfate was refluxed for 5 hours. After the temperature of the reaction mixture was returned to room temperature, under reduced pressure, the reaction mixture was concentrated and ethyl acetate was added to the concentrate, and then, the resulting mixture was washed successively with water, and then a saturated NaCl solution. The organic layer was dried over anhydrous magnesium sulfate, and the solvent was removed under reduced pressure. The residue was purified by silica gel column chromatography to obtain 442 mg (Yield: 69%) of the title compound.

$^1$H-NMR (CDCl$_3$, δ): 0.90 (3H, t, J=7 Hz), 1.21-1.62 (6H, m), 2.87 (1H, d, J=4 Hz), 3.09 (1H, dd, J=14 Hz, 7 Hz), 3.16 (1H, dd, J=14 Hz, 7 Hz), 3.59-3.63 (1H, m), 3.75 (3H, s), 4.20 (1H, dd, J=4 Hz, 4 Hz), 4.88-4.93 (1H, m), 7.00 (1H, d, J=8 Hz), 7.14 (2H, d, J=8 Hz), 7.25-7.33 (3H, m)

IR (ν, KBr, cm$^{-1}$): 2856, 2100, 1658

Reference Example 14

Synthesis of (2S,3S)-N-[(2S)-1-methoxy-1-oxo-3-phenyl-2-propyl]-3-amino-2-hydroxyheptanamide (Compound of the formula VII)

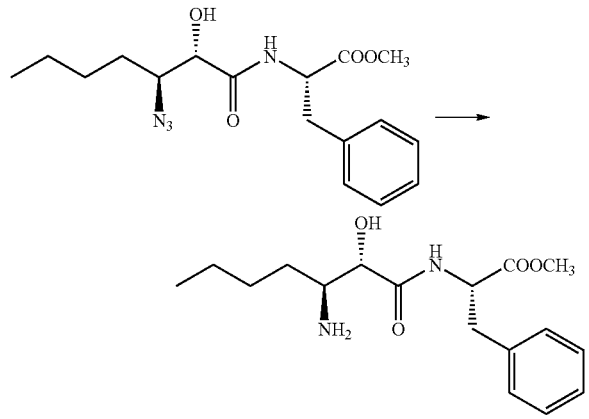

To 30 ml of a methanol solution containing 442 mg (1.27 mmol) of (2S,3S)-N-[(2S)-1-methoxy-1-oxo-3-phenyl-2-propyl]-3-azido-2-hydroxyheptanamide was added 45 mg of 5% palladium carbon, and the mixture was stirred under hydrogen atmosphere for 18 hours. Insoluble materials were filtered off, and the filtrate was distilled under reduced pressure to obtain 385 mg (Yield: 94%) of the title compound.

$^1$H-NMR (CDCl$_3$, δ): 0.89 (3H, t, J=7 Hz), 1.18-1.70 (6H, m), 2.86-2.91 (1H, m), 3.06 (1H, dd, J=14 Hz, 7 Hz), 3.18 (1H, dd, 14 Hz, 7 Hz), 3.73 (3H, s), 3.76 (1H, d, J=7 Hz), 4.86-4.92 (1H, m), 7.15 (1H, d, J=7 Hz), 7.21-7.31 (5H, m), 8.15 (1H, d, J=8 Hz)

IR (ν, KBr, cm$^{-1}$): 3364, 2956, 2860, 1652

Example 12

Synthesis of N-[(2S,3S)-2-hydroxy-1-(N-[(2S)-1-methoxy-1-oxo-3-phenyl-2-propyl]amino]-1-oxo-3-heptyl]-1-[N-(morpholine-4-carbonyl)amino]cyclohexanecarboxamide (Compound of the Formula IX)

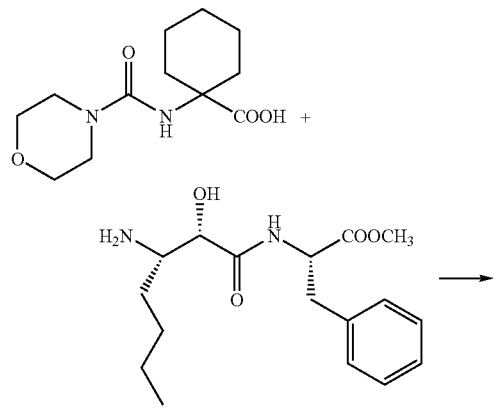

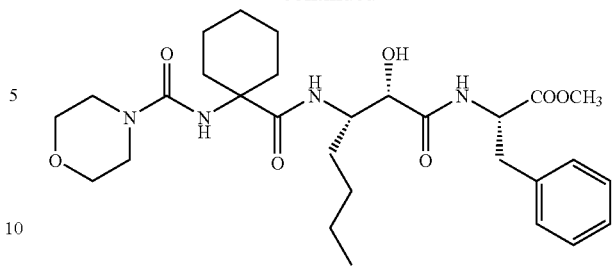

In anhydrous dichloromethane were dissolved 385 mg (1.19 mmol) of (2S,3S)-N-[(2S)-1-methoxy-1-oxo-3-phenyl-2-yl]-3-amino-2-hydroxyheptanamide, 305 mg (1.19 mmol) of 1-[N-(morpholine-4-carbonyl)amino]cyclohexanecarboxylic acid and 226 mg (1.43 mmol) of 1-hydroxybenzotriazole, and subsequently, 274 mg (1.43 mmol) of 1-ethyl-3-(3-dimethylaminopropyl) carbodiimide was added to the above mixture under nitrogen stream at 0° C. Thereafter, the temperature of the reaction mixture was returned to room temperature and the mixture was stirred overnight. The reaction mixture was concentrated under reduced pressure, the residue was dissolved in 80 ml of ethyl acetate, and the resulting mixture was washed successively with water, a 10% aqueous potassium hydrogen sulfate solution, a saturated aqueous sodium hydrogen carbonate solution and a saturated NaCl solution, dried over anhydrous magnesium sulfate, and concentrated under reduced pressure. The residue was purified by silica gel column chromatography to obtain 587 mg (Yield: 88%) of the title compound.

$^1$H-NMR (CDCl$_3$, δ): 0.86 (3H, t, J=7 Hz), 1.20-1.70 (12H, m), 1.80-1.90 (2H, m), 1.92-2.02 (2H, m), 3.05-3.17 (2H, m), 3.36 (4H, t, J=5 Hz), 3.69 (4H, t, J=5 Hz), 3.70 (3H, s), 4.09-4.14 (1H, m), 4.34 (1H, dd, J=6 Hz, 6 Hz), 4.63 (1H, s), 4.80-4.86 (1H, m), 5.00 (1H, d, J=6 Hz), 6.57 (1H, d, J=8 Hz), 7.14 (1H, d, J=8 Hz), 7.20-7.30 (5H, m)

IR (ν, KBr, cm$^{-1}$): 3392, 2932, 2860, 1658

Reference Example 15

Synthesis of N-[(S)-1,2-dioxo-1-[N-[(2S)-1-methoxy-1-oxo-3-phenyl-2-propyl]amino]-3-heptyl]-1-[N-[(morpholine-4-carbonyl)amino]cyclohexanecarboxamide (Compound of the formula X)

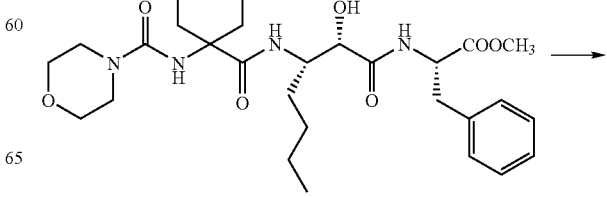

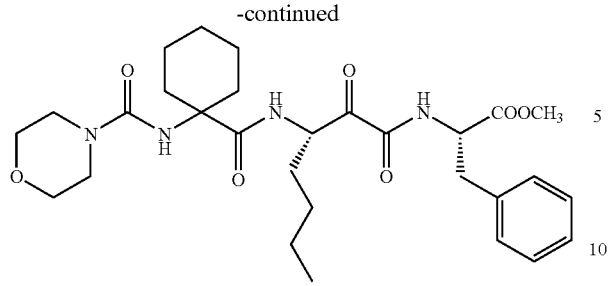

Under nitrogen stream, 814 mg (6.30 mmol) of N,N-diisopropylethylamine was added dropwise at 0° C. to a mixed solution of anhydrous dimethylsulfoxide (5 ml) and anhydrous dichloro-methane (5 ml) containing 1.00 g (6.30 mmol) of sulfur trioxide pyridine complex salt. Moreover, an anhydrous dichloromethane (5 ml) solution containing 587 mg (1.05 mmol) of N-[(2S,3S)-2-hydroxy-1-[N-[(2S)-1-methoxy-1-oxo-3-phenyl-2-propyl]-amino]-1-oxo-3-heptyl]-1-[N-(morpholine-4-carbonyl)amino]-cyclohexanecarboxamide was added to the above mixture, and the resulting mixture was stirred at 0° C. for 3 hours. After completion of the reaction, ice-water was added to the reaction mixture, and the resulting mixture was extracted with ethyl acetate. The organic layer was washed successively with a 10% aqueous citric acid solution, a saturated aqueous sodium hydrogen carbonate solution and a saturated NaCl solution, dried over anhydrous magnesium sulfate, and concentrated under reduced pressure. The residue was purified by neutral silica gel column chromatography to obtain 487 mg (Yield: 83%) of the title compound.

$^1$H-NMR (CDCl$_3$, δ): 0.87 (3H, t, J=7 Hz), 1.20-1.42 (7H, m), 1.54-1.76 (4H, m), 1.80-1.96 (3H, m), 2.05-2.18 (2H, m), 3.06-3.18 (2H, m), 3.36 (4H, t, J=5 Hz), 3.71 (4H, t, J=5 Hz), 3.72 (3H, s), 4.46 (1H, d, J=6 Hz), 4.80-4.85 (1H, m), 5.17-5.19 (1H, m), 7.09 (1H, d, J=8 Hz), 7.12 (1H, dd, J=8 Hz, 2 Hz), 7.23-7.31 (4H, m), 7.96 (1H, d, J=7 Hz)

IR (ν, KBr, cm$^{-1}$): 2932, 2860, 1678

Example 13

Synthesis of (2S)-N-[(2S,3S)-2-hydroxy-1-[N-[(1S,2S)-2-hydroxycyclohexane-1-yl]amino]-1-oxo-3-heptyl]-2-acetyloxy-3-phenylpropylamide (Compound of the formula IX)

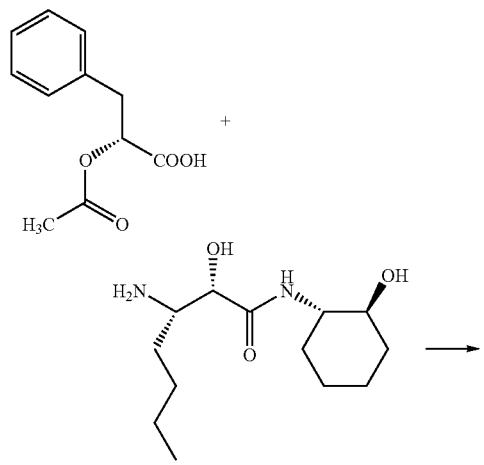

In 20 ml of dichloromethane were dissolved 1.0 g (5.5 mmol) of (S)-2-acetyloxy-3-phenylpropanoic acid, 1.4 g (5.5 mmol) of (2S,3S)-N-[(1S,2S)-2-hydroxycyclohexane-1-yl]-3-amino-2-hydroxyheptanamide and 1.0 g (6.6 mmol) of 1-hydroxybenzo-triazole, and then, 1.3 g (6.6 mmol) of 1-ethyl-3-(3-di-methylaminopropyl)carbodiimide was added to the above mixture under ice-cooling and the resulting mixture was stirred for 18 hours. The solvent was removed under reduced pressure, ethyl acetate was added to the residue, and the resulting mixture was washed successively with a 10% aqueous potassium hydrogen sulfate solution, a saturated aqueous sodium hydrogen carbonate solution and then a saturated NaCl solution, dried over an hydrous magnesium sulfate and the solvent was removed under reduced pressure. The residue was purified by silica gel column chromatography to obtain 2.2 g (Yield: 84%) of the title compound.

$^1$H-NMR (CDCl$_3$, δ): 0.84 (3H, t, J=7 Hz), 0.99-1.37 (8H, m), 1.43-1.58 (2H, m), 1.68-1.74 (2H, m), 2.01-2.10 (1H, m), 2.07 (3H, s), 3.10 (1H, dd, J=14 Hz, 7 Hz), 3.17 (1H, dd, J=14 Hz, 6 Hz), 3.38 (1H, dt, J=10 Hz, 4 Hz), 3.55-3.62 (1H, m), 3.97-4.03 (1H, m), 4.16 (1H, s), 4.97 (1H, brs), 5.24 (1H, dd, J=7 Hz, 6 Hz), 6.35 (1H, d, J=8 Hz), 6.93 (1H, d, J=8 Hz), 7.18-7.31 (5H, m)

IR (ν, KBr, cm$^{-1}$): 3314, 2935, 1671, 1636

Reference Example 16

Synthesis of (2S)—N-[(S)-1,2-dioxo-1-[N-[(S)-2-oxocyclo-hexyl]amino]-3-heptyl]-2-acetyloxy-3-phenylpropylamide (Compound of the formula X)

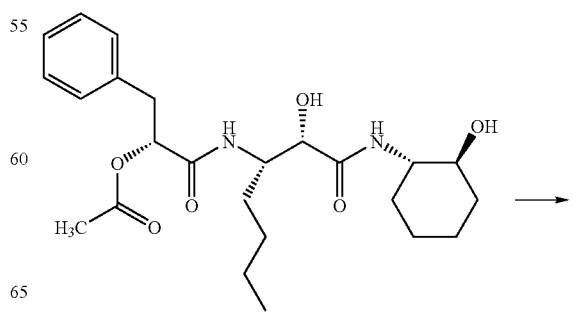

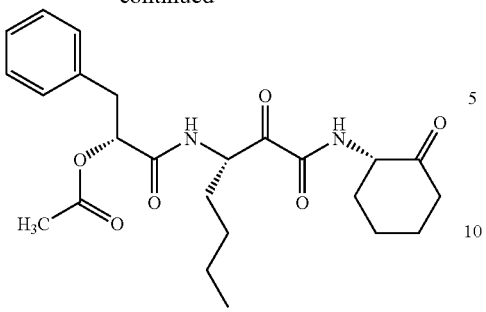
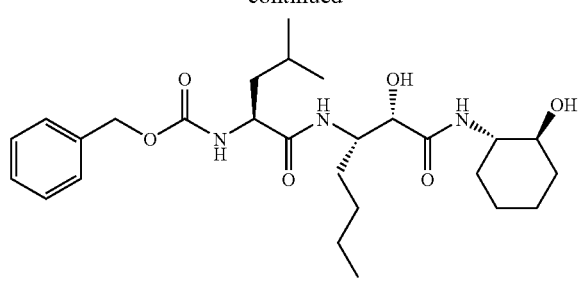

Under nitrogen stream, 700 mg (5.4 mmol) of N,N-diisopropylethylamine was added dropwise at 0° C. to a mixed solution of anhydrous dimethylsulfoxide (20 ml) and anhydrous dichloromethane (15 ml) containing 854 mg (5.4 mmol) of sulfur trioxide pyridine complex salt. Moreover, an anhydrous dichloromethane (5 ml) solution containing 200 mg (0.45 mmol) of (2S)-N-[(2S,3S)-2-hydroxy-1-[N-[(1S,2S)-2-hydroxycyclo-hexane-1-yl]amino]-1-oxo-3-heptyl]-2-acetyloxy-3-phenyl-propylamide was added to the above mixture, and the resulting mixture was stirred at 0° C. for 3 hours. After completion of the reaction, ice-water was added to the reaction mixture, and the resulting mixture was extracted with ethyl acetate. The organic layer was washed successively with a 10% aqueous citric acid solution, a saturated aqueous sodium hydrogen carbonate solution and a saturated NaCl solution, dried over anhydrous magnesium sulfate, and concentrated under reduced pressure. The residue was washed with ether to obtain 115 mg (Yield: 58%) of the title compound.

$^1$H-NMR (CDCl$_3$, δ): 0.85 (3H, t, J=7 Hz), 1.10-1.94 (10H, m), 2.10 (3H, s), 2.15-2.20 (1H, m), 2.43 (1H, dt, J=13 Hz, 6 Hz), 2.56-2.68 (2H, m), 3.07 (1H, dd, J=14 Hz, 7 Hz), 3.32 (1H, dd, J=14 Hz, 5 Hz), 4.38-4.44 (1H, m), 5.26 (1H, dt, J=8 Hz, 5 Hz), 5.39 (1H, dd, J=7 Hz, 5 Hz), 6.55 (1H, d, J=8 Hz), 7.16-7.29 (5H, m), 7.75 (1H, d, J=6 Hz)

IR (ν, KBr, cm$^{-1}$): 3334, 2934, 2862, 1740, 1671

Example 14

Synthesis of (2S)-N-[(2S,3S)-2-hydroxy-1-[N-[(1S,2S)-2-hydroxycyclohexane-1-yl]amino]-1-oxo-3-heptyl]-4-methyl-2-[N-(phenylmethoxycarbonyl)amino]pentanamide (Compound of the Formula IX)

Under argon gas stream, to 25 ml of an anhydrous tetrahydrofuran solution containing 761 mg (1.1 mmol) of L-N-phenylmethoxycarbonyl leucine were successively added dropwise at 0° C. 0.23 ml (1.9 mmol) of pivaloyl chloride, and then, 40 ml of an anhydrous tetrahydrofuran-chloroform (5:3) suspension containing 400 mg (1.5 mmol) of (2S,3S)-N-[(1S,2S)-2-hydroxycyclohexane-1-yl]-3-amino-2-hydroxyheptanamide, and the resulting mixture was stirred at the same temperature for 2 hours. Moreover, the temperature of the reaction mixture was returned to room temperature and the mixture was stirred for 10 hours. After completion of the reaction, to the reaction mixture was added 30 ml of a saturated aqueous ammonium chloride solution, and tetrahydrofuran and chloroform were removed by distillation. The residue was extracted with 50 ml of 5%-methanol/chloroform three times. The organic layers were combined, washed with 100 ml of a saturated aqueous sodium hydrogen carbonate solution and then 100 ml of a saturated NaCl solution, dried over anhydrous sodium sulfate, and then concentrated under reduced pressure. The residue was recrystallized from 35 ml of ethanol-diethyl ether (5:2) to obtain 210 mg (Yield: 26.8%) of the title compound.

$^1$H-NMR (DMSO-d$_6$, δ): 0.79 (3H, t, J=7 Hz), 0.85 (3H, d, J=7 Hz), 0.87 (3H, d, J=7 Hz), 1.04-1.31 (9H, m), 1.34-1.50 (3H, m), 1.52-1.66 (3H, m), 1.76-1.87 (2H, m), 3.26-3.42 (2H, m), 3.84 (1H, dd, J=6 Hz, 3 Hz), 4.00-4.13 (2H, m), 4.51 (1H, d, J=5 Hz), 5.02 (2H, s), 5.71 (1H, d, J=6 Hz), 7.28-7.40 (6H, m), 7.43 (1H, d, J=8 Hz), 7.47 (1H, d, J=9 Hz)

IR (ν, KBr, cm$^{-1}$): 3322, 2937, 1660, 1531

Reference Example 17

Synthesis of (2S)-N-[(S)-1,2-dioxo-1-[N-[(S)-2-oxocyclo-hexyl]amino]-3-heptyl]-4-methyl-2-[N-(phenylmethoxycarbon-yl)amino]pentanamide (Compound of the formula X)

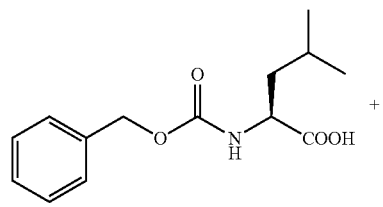

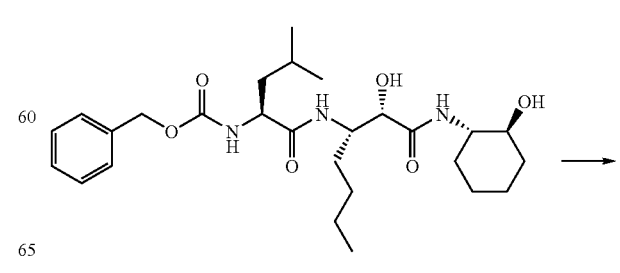

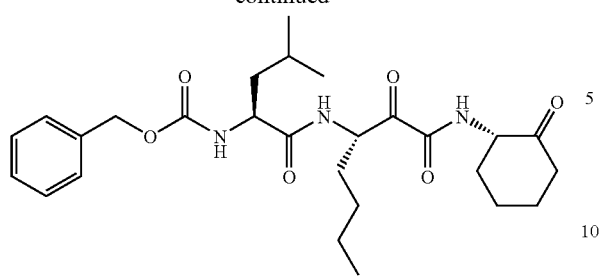

Under argon gas stream, to 4 ml of an anhydrous dimethylsulfoxide-dichloromethane (1:1) solution containing 567 mg (3.6 mmol) of sulfur trioxide pyridine complex salt were successively added dropwise at 0° C. 0.62 ml (3.6 mmol) of diisopropylethylamine, and then, 2 ml of an anhydrous dimethylsulfoxide solution containing 150 mg (0.3 mmol) of (2S)-N-[(2S,3S)-2-hydroxy-1-[N-[(1S,2S)-2-hydroxycyclohexane-1-yl]amino]-1-oxo-3-heptyl]-4-methyl-2-[N-(phenylmethoxycarbonyl)amino]pentanamide, and the mixture was stirred at the same temperature for 5 hours. After completion of the reaction, 25 ml of ice-water was added to the reaction mixture, and the resulting mixture was extracted with 20 ml of ethylacetate three times. The organic layers were combined, washed successively with 50 ml of a 10%-aqueous citric acid solution, 50 ml of a saturated aqueous sodium hydrogen carbonate solution, and then 50 ml of a saturated NaCl solution, dried over anhydrous sodium sulfate, and then, concentrated under reduced pressure. The residue was applied to neutral silica gel column chromatography, and eluted by a hexane-ethyl acetate (11:9) eluent to obtain 120 mg of the title compound, and further recrystallized from 5 ml of ethyl acetate-hexane (3:2) to obtain 90 mg (Yield: 60.5%) of the title compound.

$^1$H-NMR (CDCl$_3$, δ): 0.87 (3H, t, J=7 Hz), 0.94 (6H, d, J=6 Hz), 1.20-1.55 (6H, m), 1.58-1.74 (4H, m), 1.74-1.87 (1H, m), 1.87-2.00 (2H, m), 2.12-2.21 (1H, m), 2.40 (1H, dt, J=14 Hz, 6 Hz), 2.53-2.61 (1H, m), 2.61-2.70 (1H, m), 4.16-4.25 (1H, m), 4.37-4.45 (1H, m), 5.08-5.18 (3H, m), 5.28 (1H, dt, J=8 Hz, 5 Hz), 6.54 (1H, d, J=8 Hz), 7.29-7.40 (5H, m), 7.77 (1H, d, J=6 Hz)

IR (ν, KBr, cm$^{-1}$): 3320, 1689, 1661, 1526

Example 15

Synthesis of (2S)-N-[(2S,3S)-2-hydroxy-1-[N-[(1S,2S)-2-hydroxycyclohexane-1-yl]amino]-1-oxo-3-heptyl]-1-(phenylmethoxycarbonyl)pyrrolidin-2-carboxamide (Compound of the Formula IX)

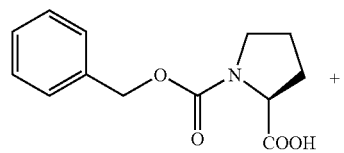 +

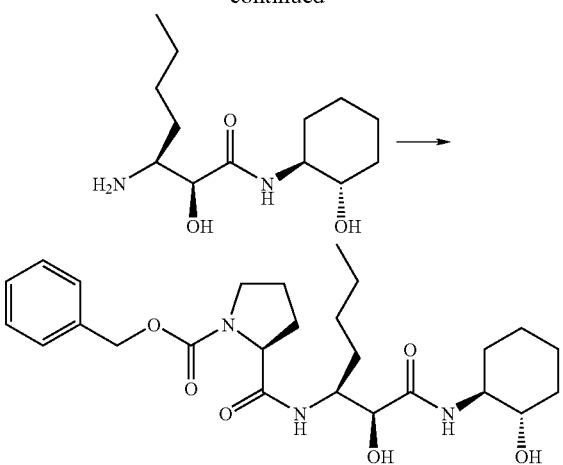

In 20 ml of dimethylformamide were dissolved 523 mg (2.1 mmol) of L-N-phenylmethoxycarbonylproline, 518 mg (2.0 mmol) of (2S,3S)-N-[(1S,2S)-2-hydroxycyclohexane-1-yl]-3-amino-2-hydroxyheptanamide and 338 mg (2.2 mmol) of 1-hydroxy-benzotriazole, and under ice-cooling, 423 mg (2.2 mmol) of 1-ethyl-3-(3-dimethylaminopropyl) carbodiimide was added to the above solution and the resulting mixture was stirred for 18 hours. To the reaction mixture was added 1N hydrochloric acid, and the resulting mixture was extracted with chloroform. The organic layer was washed with a saturated aqueous sodium hydrogen carbonate solution and then a saturated NaCl solution, dried over anhydrous magnesium sulfate, and the solvent was removed under reduced pressure. The residue was purified by silica gel column chromatography to obtain 709 mg (Yield: 72%) of the title compound.

$^1$H-NMR (DMSO-d$_6$, δ): 0.68 (1.8H, t, J=7 Hz), 0.80 (1.2H, t, J=7 Hz), 0.94-1.44 (10H, m), 1.52-1.64 (2H, m), 1.74-1.94 (5H, m), 1.97-2.18 (1H, m), 3.26-3.49 (4H, m), 3.81-3.86 (1H, m), 4.00-4.09 (1H, m), 4.23 (0.4H, dd, J=8 Hz, 3 Hz), 4.30 (0.6H, dd, J=8 Hz, 3 Hz), 4.50 (1H, d, J=5 Hz), 4.93-5.11 (2H, m), 5.70 (0.4H, d, J=5 Hz), 5.75 (0.6H, d, J=5 Hz), 7.24-7.40 (6H, m), 7.62 (0.4H, d, J=9 Hz), 7.70 (0.6H, d, J=9 Hz)

IR (ν, KBr, cm$^{-1}$): 3401, 2933, 1664, 1637

Reference Example 18

Synthesis of (2S)-N-[(S)-1,2-dioxo-1-[N-[(S)-2-oxocyclohexyl]amino]-3-heptyl]-1-(phenylmethoxycarbonyl)pyrrolidine-2-carboxamide (Compound of the formula X)

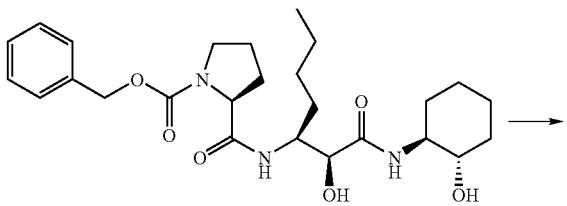

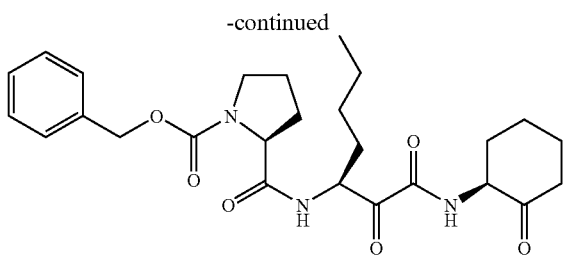

Under argon gas stream, to 10 ml of an anhydrous dimethylsulfoxide-dichloromethane (1:1) solution containing 1.38 g (8.6 mmol) of sulfur trioxide pyridine complex salt were successively added dropwise at 0° C. 1.47 ml (8.6 mmol) of diisopropylethylamine, and then, 5 ml of an anhydrous dimethylsulfoxide solution containing 350 mg (0.7 mmol) of (2S)-N-[(2S,3S)-2-hydroxy-1-[N-[(1S,2S)-2-hydroxycyclohexane-1-yl]amino]-1-oxo-3-heptyl]-1-(phenylmethoxycarbonyl)pyrrolidine-2-carboxamide, and the resulting mixture was stirred at the same temperature for 5 hours. After completion of the reaction, to the reaction mixture was added 25 ml of ice-water, and the resulting mixture was extracted with 30 ml of ethylacetate three times. The organic layers were combined, washed with 100 ml of a 10%-aqueous citric acid solution, 100 ml of a saturated aqueous sodium hydrogen carbonate solution, and then, 100 ml of a saturated NaCl solution, dried over anhydrous sodium sulfate, and then, concentrated under reduced pressure. The residue was purified by neutral silica gel column chromatography to obtain 300 mg (Yield: 86.1%) of the title compound.

$^1$H-NMR (DMSO-d$_6$, δ): 0.77 (1.8H, t, J=7 Hz), 0.86 (1.2H, t, J=7 Hz), 1.12-1.58 (6H, m), 1.63-1.92 (7H, m), 1.96-2.05 (1H, m), 2.07-2.24 (2H, m), 2.27-2.34 (1H, m), 2.48-2.58 (1H, m), 3.32-3.48 (2H, m), 4.28 (0.4H, dd, J=9 Hz, 3 Hz), 4.33 (0.6H, dd, J=9 Hz, 3 Hz), 4.39-4.47 (1H, m), 4.95 (1H, ddd, J=9 Hz, 7 Hz, 3 Hz), 4.99-5.11 (2H, m), 7.25-7.40 (5H, m), 8.28 (0.4H, d, J=7 Hz), 8.32 (0.6H, d, J=7 Hz), 8.53 (0.4H, d, J=8 Hz), 8.55 (0.6H, d, J=8 Hz)

IR (ν, KBr, cm$^{-1}$): 3320, 2935, 2863, 1704, 1666

Utilizability in Industry

According to the present invention, a novel epoxycarboxamide compound, azide compound and aminoalcohol compound and a process for preparing an α-keto amide compound using them can be provided, and said novel compounds can be used as manufacturing intermediates which can be led to a useful α-ketoamide compound having a protease-inhibiting activity extremely economically and stereoselectively.

The invention claimed is:

1. An azide compound represented by the following formula (VI):

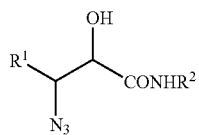

(VI)

wherein R$^1$ represents a methyl group, an ethyl group, a n-propyl group, a 1-methylethyl group, a n-butyl group, a 2-methylpropyl group, or a 1-methylpropyl group; and R$^2$ represents a substituted or unsubstituted, straight, branched or cyclic alkyl group having 1 to 12 carbon atoms, a substituted or unsubstituted, straight, branched or cyclic alkenyl group having 2 to 6 carbon atoms, a substituted or unsubstituted aromatic hydrocarbon group or a substituted or unsubstituted heterocyclic group having at least one hetero atom selected from a nitrogen atom, a sulfur atom, and an oxygen atom with a 5- or 6-membered ring, or selected from a hexahydro-2-azepine-3-yl group, a perhydro-4-azcpine-1-yl group, and a perhydro-4-aazepine-1-yl group, where the substituent for the alkyl group, alkenyl group, aromatic hydrocarbon group or heterocyclic group is a hydroxyl group, an oxo group, a halogen atom, a straight, branched or cyclic alkenyl group having 2 to 6 carbon atoms, an aromatic hydrocarbon group, a heterocyclic group, a nitro group, an amino group, a sulfonyl group, an alkoxy group, an alkylthio group, an aryloxy group, an arylthio group, an acyl group, an alkoxycarbonyl group, a carbamoyl group substituted by an alkyl group, alkenyl group, aromatic hydrocarbon group, heterocyclic group, or amino group, a sulfonamide group substituted by an alkyl group, alkenyl group, aromatic hydrocarbon group, heterocyclic group, or amino group, an amide group substituted by a phenoxy group, 1-napthyloxy group, 2-naptliyloxy group, alkyl group, alkenyl group, aromatic hydrocarbon group, heterocyclic group, amino group, alkoxy group, mercapto group, cyano group, or methylenedioxy group.

2. The azide compound according to claim 1, wherein the compound represented by the formula (VI) is a compound represented by the following formula (VIa):

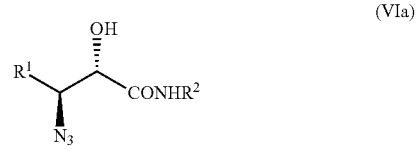

(VIa)

wherein R$^1$ and R$^2$ have the same meanings as defined above.

3. The azide compound according to claim 1, wherein the compound represented by the formula (VI) is a compound represented by the following formula (VIb):

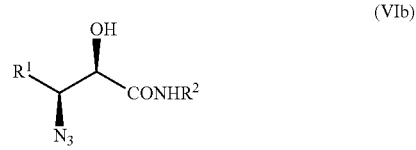

(VIb)

wherein R$^1$ and R$^2$ have the same meanings as defined above.

4. The azide compound according to claim 1, wherein the compound represented by the formula (VI) is a compound represented by the following formula (VIc):

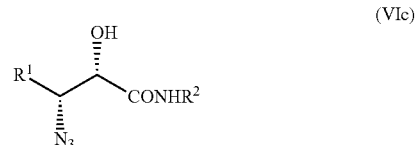

(VIc)

wherein R$^1$ and R$^2$ have the same meanings as defined above.

5. The azide compound according to claim 1, wherein the compound represented by the formula (VI) is a compound represented by the following tbrmula (VId):

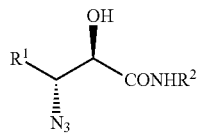

wherein $R^1$ and $R^2$ have the same meanings as defined above.

6. The azide compound according to claim 1, wherein $R^1$ is a n-butyl group.

7. The azide compound according to claim 1, wherein $R^2$ is a substituted or unsubstituted cyclic alkyl group.

8. The azide compound according to claim 7, wherein $R^2$ is a substituted or unsubstituted cyclohexyl group.

9. The azide compound according to claim 7, wherein a substituent for the cyclic alkyl group of $R^2$ is a hydroxy group.

10. The azide compound according to claim 9, wherein $R^2$ is represented by the following formula:

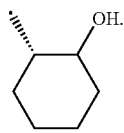

11. The azide compound according to claim 1, wherein $R^2$ is a methoxyoxophenylpropyl group or a methylenedioxyphenyl group.

* * * * *